United States Patent
Allec et al.

(10) Patent No.: US 11,857,298 B1
(45) Date of Patent: Jan. 2, 2024

(54) DEVICES HAVING MATTER DIFFERENTIATION DETECTORS

(71) Applicant: Apple Inc., Cupertino, CA (US)

(72) Inventors: Nicholas P. Allec, Champaign, IL (US); Albert E. Cerussi, San Jose, CA (US); Maximillian C. Bruggeman, San Jose, CA (US); Xiyu Duan, San Jose, CA (US); Ueyn L. Block, Menlo Park, CA (US)

(73) Assignee: Apple Inc., Cupertino, CA (US)

( * ) Notice: Subject to any disclaimer, the term of this patent is extended or adjusted under 35 U.S.C. 154(b) by 453 days.

(21) Appl. No.: 17/013,217

(22) Filed: Sep. 4, 2020

Related U.S. Application Data

(60) Provisional application No. 62/897,127, filed on Sep. 6, 2019.

(51) Int. Cl.
*A61B 5/024* (2006.01)
*G04B 47/06* (2006.01)
(Continued)

(52) U.S. Cl.
CPC .......... *A61B 5/02416* (2013.01); *A61B 5/681* (2013.01); *G04B 47/063* (2013.01); *G06F 1/163* (2013.01)

(58) Field of Classification Search
CPC ..... A61B 5/02416; A61B 5/681; A61B 5/145; G04B 47/063; G06F 1/163
See application file for complete search history.

(56) References Cited

U.S. PATENT DOCUMENTS

| | | |
|---|---|---|
| 4,913,150 A | 4/1990 | Cheung et al. |
| 6,313,612 B1 | 11/2001 | Honda |
| | (Continued) | |

FOREIGN PATENT DOCUMENTS

| | | |
|---|---|---|
| CN | 103876726 | 6/2014 |
| CN | 203943664 | 11/2014 |
| | (Continued) | |

OTHER PUBLICATIONS

U.S. Appl. No. 16/812,152, filed Mar. 6, 2020, Mehra et al.
(Continued)

*Primary Examiner* — Eric F Winakur
*Assistant Examiner* — Abid A Mustansir
(74) *Attorney, Agent, or Firm* — Brownstein Hyatt Farber Schreck, LLP

(57) ABSTRACT

A wearable device includes a housing; a wrist band attached to the housing; first and second emitters positioned within the housing and configured to respectively emit, through a back of the housing, a first beam of electromagnetic radiation having a first infrared (IR) wavelength and a second beam of electromagnetic radiation having a second IR wavelength. The second IR wavelength is different from the first IR wavelength. The wearable device also includes a photodetector positioned within the housing and filtered to detect a set of electromagnetic radiation wavelengths including the first IR wavelength and the second IR wavelength; and a matter differentiation circuit configured to indicate, at least partly in response to signals indicating amounts of the first IR wavelength and the second IR wavelength received by the photodetector, whether the back of the housing is likely proximate to human tissue.

22 Claims, 18 Drawing Sheets

(51) Int. Cl.
*A61B 5/00* (2006.01)
*G06F 1/16* (2006.01)

(56) References Cited

U.S. PATENT DOCUMENTS

| | | | |
|---|---|---|---|
| 6,526,300 B1 * | 2/2003 | Kiani | A61B 5/14552 |
| | | | 600/344 |
| 6,882,874 B2 | 4/2005 | Huiku | |
| 8,463,345 B2 | 6/2013 | Kuhn et al. | |
| 9,226,663 B2 | 1/2016 | Fei | |
| 9,558,336 B2 | 1/2017 | Lee | |
| 9,597,014 B2 | 3/2017 | Venkatraman et al. | |
| 9,743,838 B2 | 8/2017 | Richards | |
| 9,763,607 B1 | 9/2017 | Acosta et al. | |
| 10,032,557 B1 | 7/2018 | Bossetti | |
| 10,092,197 B2 | 10/2018 | Han | |
| 10,117,587 B2 | 11/2018 | Han | |
| 10,178,959 B1 | 1/2019 | Homyk | |
| 10,181,021 B2 | 1/2019 | Verkatraman et al. | |
| 10,188,330 B1 * | 1/2019 | Kadlec | A61B 5/1495 |
| 10,241,476 B1 | 3/2019 | Moten | |
| 10,417,513 B2 | 9/2019 | Lee | |
| 10,433,739 B2 | 10/2019 | Weekly et al. | |
| 10,444,067 B2 | 10/2019 | Hsu et al. | |
| 10,485,437 B2 | 11/2019 | Wei et al. | |
| 10,485,478 B1 | 11/2019 | Mirov | |
| 10,586,525 B1 | 2/2020 | Wu et al. | |
| 10,627,783 B2 | 4/2020 | Rothkopf | |
| 10,760,955 B2 | 9/2020 | Chu et al. | |
| 10,966,643 B1 | 5/2021 | Vavadi | |
| 11,018,524 B2 | 5/2021 | Simpson | |
| 2002/0082489 A1 * | 6/2002 | Casciani | A61B 5/14542 |
| | | | 600/323 |
| 2005/0049469 A1 * | 3/2005 | Aoyagi | A61B 5/14551 |
| | | | 600/323 |
| 2014/0275852 A1 * | 9/2014 | Hong | A61B 5/0002 |
| | | | 600/479 |
| 2015/0054348 A1 | 2/2015 | Akiya | |
| 2015/0099943 A1 | 4/2015 | Russell | |
| 2016/0129279 A1 | 5/2016 | Ferolito | |
| 2016/0278712 A1 | 9/2016 | Sagara | |
| 2017/0095216 A1 | 4/2017 | Laty | |
| 2017/0135633 A1 * | 5/2017 | Connor | A61N 1/36557 |
| 2017/0172476 A1 | 6/2017 | Schilthuizen | |
| 2017/0251963 A1 | 9/2017 | Hashimoto et al. | |
| 2017/0311825 A1 * | 11/2017 | Weekly | A61B 5/6814 |
| 2017/0315511 A1 | 11/2017 | Shim et al. | |
| 2018/0014781 A1 * | 1/2018 | Clavelle | A61B 5/681 |
| 2018/0020960 A1 * | 1/2018 | Sarussi | G01N 33/4925 |
| | | | 600/310 |
| 2018/0085040 A1 | 3/2018 | Ferber et al. | |
| 2018/0098708 A1 | 4/2018 | Lee | |
| 2018/0344175 A1 | 12/2018 | Rulkov et al. | |
| 2019/0072912 A1 | 3/2019 | Pandya et al. | |
| 2019/0090766 A1 | 3/2019 | Block et al. | |
| 2019/0090806 A1 | 3/2019 | Clavelle et al. | |
| 2019/0167124 A1 | 6/2019 | Verkruijsse et al. | |
| 2019/0192076 A1 * | 6/2019 | McHale | A61B 5/7445 |
| 2019/0246967 A1 * | 8/2019 | Pekander | A61B 5/14552 |
| 2020/0163616 A1 | 5/2020 | Sakaya | |
| 2021/0093237 A1 | 4/2021 | Venugopal et al. | |
| 2021/0278561 A1 | 9/2021 | Mehra et al. | |
| 2022/0085231 A1 | 3/2022 | Liu et al. | |

FOREIGN PATENT DOCUMENTS

| | | |
|---|---|---|
| CN | 109589095 | 4/2019 |
| CN | 109645972 | 4/2019 |
| EP | 3451117 | 3/2019 |
| KR | 20180042472 | 4/2018 |

OTHER PUBLICATIONS

U.S. Appl. No. 17/018,920, filed Sep. 11, 2020, Allec et al.
U.S. Appl. No. 17/018,985, filed Sep. 11, 2020, Shaga et al.
U.S. Appl. No. 17/020,659, filed Sep. 14, 2020, Duan et al.
U.S. Appl. No. 17/473,745, filed Sep. 13, 2021, Liu et al.

* cited by examiner

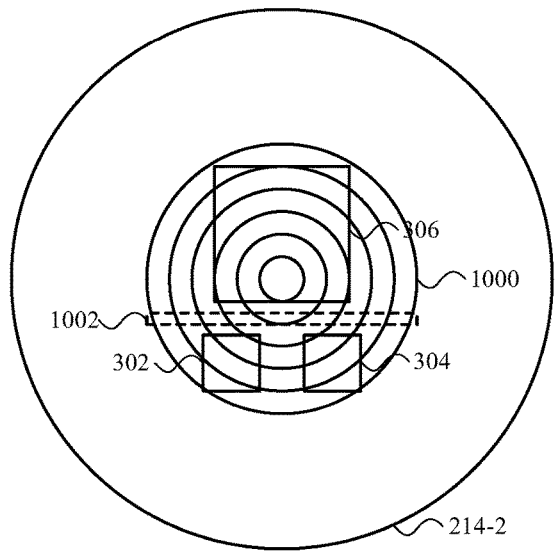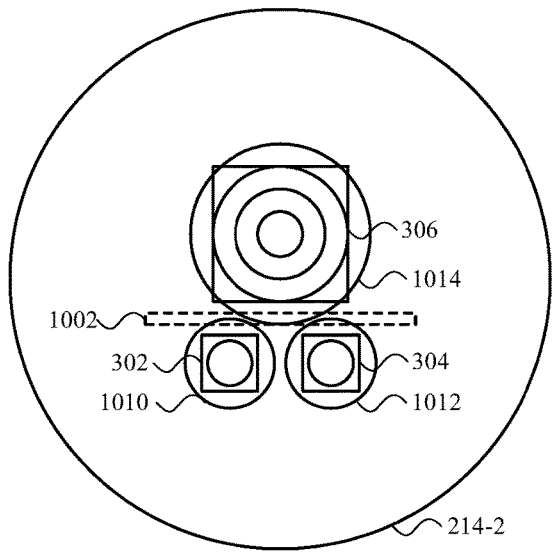
*FIG. 10A*  *FIG. 10B*
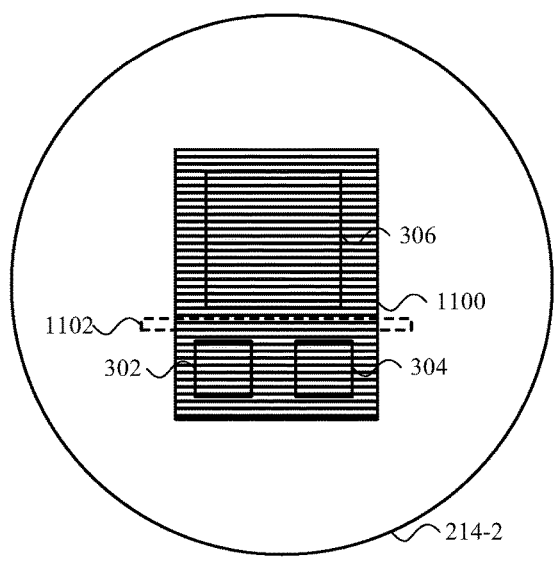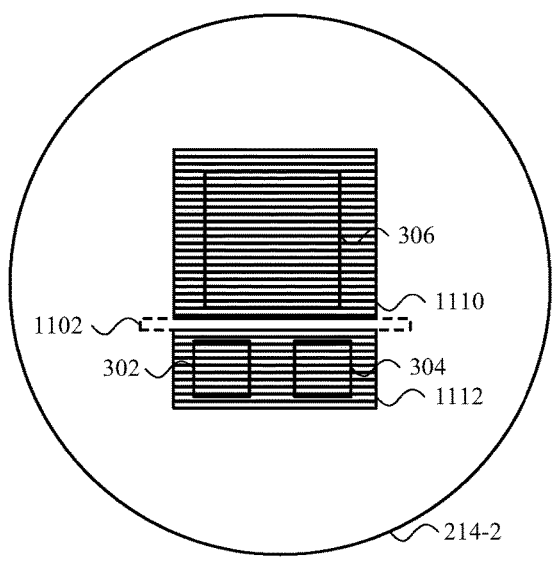
*FIG. 11A*  *FIG. 11B*

DEVICES HAVING MATTER DIFFERENTIATION DETECTORS

CROSS-REFERENCE TO RELATED APPLICATION

This application is a nonprovisional of and claims the benefit under 35 U.S.C. § 119(e) of U.S. Provisional Patent Application No. 62/897,127, filed Sep. 6, 2019, and entitled "Devices Having Human Tissue and/or Object Proximity Detectors," the contents of which are hereby incorporated by reference as if fully disclosed herein.

FIELD

The described embodiments generally relate to devices such as wearable devices (e.g., an electronic watch) and, more particularly, to devices having human tissue detectors and/or object proximity detectors.

BACKGROUND

Sensor systems are included in many of today's electronic devices, including electronic devices such as smartphones, computers (e.g., tablet computers or laptop computers), wearable electronic devices (e.g., electronic watches, smart watches, health monitors, audio devices, gaming devices, AR/VR devices, and so on, attached to a wrist, arm, thigh, neck or other body part of a user by one or more of bands, straps, cuffs, and so on), game controllers, navigation systems (e.g., vehicle navigation systems or robot navigation systems), and so on. Sensor systems may variously sense the presence of objects, distances to objects, proximities of objects, movements of objects (e.g., whether objects are moving, or the speed, acceleration, or direction of movement of objects), and so on. Sensor systems may also identify sounds made by an object or person, sounds made by an object or person interacting with its environment, or sounds made by an object or person interacting with a sensor system or device in which the sensor system is housed.

Given the wide range of sensor system applications, any new development in the configuration or operation of a sensor system can be useful. New developments that may be particularly useful are developments that reduce the cost, size, complexity, part count, or manufacture time of the sensor system, or developments that improve the sensitivity or speed of sensor system operation.

SUMMARY

Embodiments of the systems, devices, methods, and apparatus described in the present disclosure are directed to the configuration and operation of a device that includes one or more human tissue detectors and/or object proximity detectors.

In a first aspect, the present disclosure describes a wearable device. The wearable device may include a housing; a wrist band attached to the housing; a first emitter positioned within the housing and configured to emit, through a back of the housing, a first beam of electromagnetic radiation having a first infrared (IR) wavelength; and a second emitter positioned within the housing and configured to emit, through the back of the housing, a second beam of electromagnetic radiation having a second IR wavelength. The second IR wavelength may be different from the first IR wavelength. The wearable device may also include a photodetector positioned within the housing and filtered to detect a set of electromagnetic radiation wavelengths including the first IR wavelength and the second IR wavelength; and a matter differentiation circuit configured to indicate, at least partly in response to signals indicating amounts of the first IR wavelength and the second IR wavelength received by the photodetector, whether the back of the housing is likely proximate to human tissue.

In a second aspect, the present disclosure describes a device. The device may include a first emitter configured to emit a first beam of electromagnetic radiation toward an object, and a second emitter configured to emit a second beam of electromagnetic radiation toward an object. The first beam of electromagnetic radiation and the second beam of electromagnetic radiation may have different human tissue reflectance factors. The device may also include a photodetector filtered to detect reflections or backscatters of the first beam and the second beam; a timing circuit configured to operate the first emitter and the second emitter, to respectively emit the first beam of electromagnetic radiation or the second beam of electromagnetic radiation at different times; and a matter differentiation circuit configured to indicate whether the device is likely proximate to human tissue, the indication based at least partly on a first amount of electromagnetic radiation received by the photodetector after the first emitter emits the first beam, and a second amount of electromagnetic radiation received by the photodetector after the second emitter emits the second beam.

In addition to the exemplary aspects and embodiments described above, further aspects and embodiments will become apparent by reference to the drawings and by study of the following description.

BRIEF DESCRIPTION OF THE DRAWINGS

The disclosure will be readily understood by the following detailed description in conjunction with the accompanying drawings, wherein like reference numerals designate like structural elements, and in which:

FIG. 10A shows an example plan view of a Fresnel lens positioned over a group of sensing components including the emitters and photodetector described with reference to FIGS. 3A-3B;

FIG. 10B shows an example plan view of a set of Fresnel lenses, with each of the Fresnel lenses positioned over a respective sensing component of a group of sensing components;

FIG. 11A shows an example plan view of an LCF positioned over a group of sensing components including the emitters and photodetector described with reference to FIGS. 3A-3B;

FIG. 11B shows an example plan view of different LCFs positioned over different sets of the sensing components described with reference to FIGS. 3A-3B;

Figure 1:
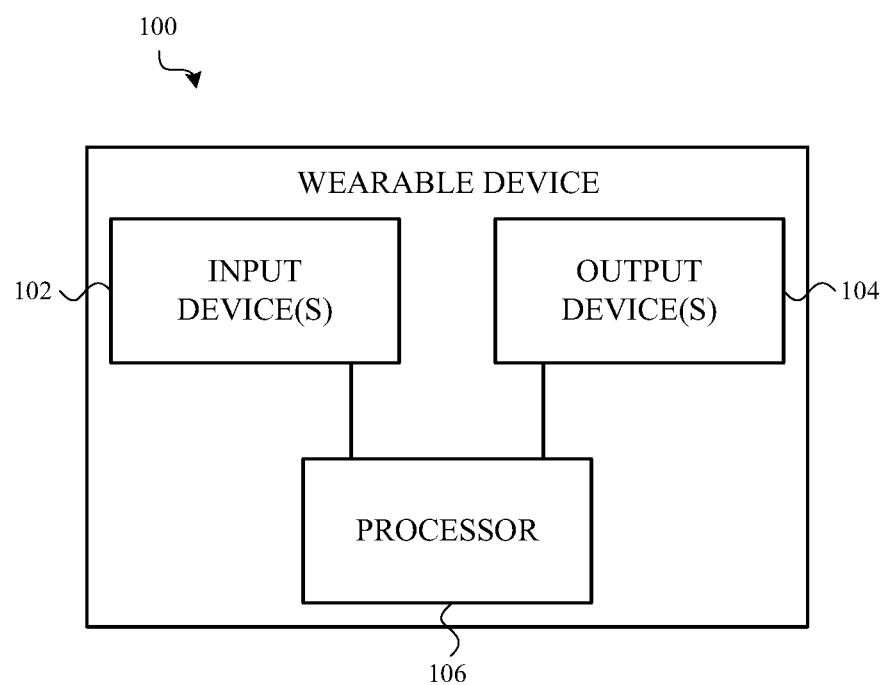
FIG. 1 shows a functional block diagram of a device.

The use of cross-hatching or shading in the accompanying figures is generally provided to clarify the boundaries between adjacent elements and also to facilitate legibility of the figures. Accordingly, neither the presence nor the absence of cross-hatching or shading conveys or indicates any preference or requirement for particular materials, material properties, element proportions, element dimensions, commonalities of similarly illustrated elements, or any other characteristic, attribute, or property for any element illustrated in the accompanying figures.

Additionally, it should be understood that the proportions and dimensions (either relative or absolute) of the various features and elements (and collections and groupings thereof) and the boundaries, separations, and positional relationships presented therebetween, are provided in the accompanying figures merely to facilitate an understanding of the various embodiments described herein and, accordingly, may not necessarily be presented or illustrated to scale, and are not intended to indicate any preference or requirement for an illustrated embodiment to the exclusion of embodiments described with reference thereto.

DETAILED DESCRIPTION

Reference will now be made in detail to representative embodiments illustrated in the accompanying drawings. It should be understood that the following description is not intended to limit the embodiments to one preferred embodiment. To the contrary, it is intended to cover alternatives, modifications, and equivalents as can be included within the spirit and scope of the described embodiments as defined by the appended claims.

Some aspects of the following description relate to differentiating the types of matter that are proximate to a device. For example, in the context of a wearable device (e.g., electronic watches, smart watches, health monitors, audio devices, gaming devices, AR/VR devices, and so on, attached to a wrist, arm, thigh, neck or other body part of a user by one or more of bands, straps, cuffs, and so on), the systems, devices, methods, and apparatus described herein may be used to differentiate when the device is likely proximate to human tissue versus when the device is likely proximate to something else (e.g., a wood, polymer (e.g., plastic), glass, and/or ceramic material or surface). In some cases, the matter differentiation may be performed by emitting a first beam of electromagnetic radiation having a first IR wavelength through a back of the device, and emitting a second beam of electromagnetic radiation having a second IR wavelength through the back of the device. The first and second IR wavelengths may be selected such that the first IR wavelength has a first human tissue reflectance factor, and the second IR wavelength has a second human tissue reflectance factor. For example, the first IR wavelength may have a higher human tissue reflectance factor than the second IR wavelength, such that the first IR wavelength reflects from human tissue more readily and is absorbed by human tissue to a lesser degree than the first IR wavelength. The first and second IR wavelengths may also be selected such that the first and second IR wavelengths both have a high reflectance factor for other materials or surfaces, such as wood, polymer (e.g., plastic), glass, and/or ceramic materials or surfaces.

In some of the described embodiments, the first beam of electromagnetic radiation may be emitted through the back of the device, and an amount of electromagnetic radiation having the first IR wavelength, that is reflected or backscattered back toward the device, may be measured. The second beam of electromagnetic radiation may also be emitted through the back of the device, and an amount of electromagnetic radiation having the second IR wavelength, that is reflected or backscattered back toward the device, may be measured. A ratio of the first amount of electromagnetic radiation to the second amount of electromagnetic radiation, or difference between the first and second amounts of electromagnetic radiation may be determined, and the ratio or difference may be compared to a threshold, or to various ratios or differences that have been computed for different types of matter. The type of matter to which the device is likely proximate may then be determined using a result (or results) of the comparison(s).

In some embodiments, a processor or other circuitry may be configured to perform (or not perform) various operations depending on whether the device is determined to likely be proximate human tissue In the context of a seat, the matter differentiation described herein may be used, for example, to determine whether a person is likely sitting in the seat. In the context of a button, the matter differentiation described herein may be used, for example, to determine whether a user is pressing the button. In the context of an earbud, headphones, or a gaming device (e.g., a set of goggles or glove), the matter differentiation described herein may be used, for example, to determine whether the earbud, headphones, or gaming device is being worn.

Some aspects of the following description relate to determining the proximity of a device to an object using a first proximity sensor, when possible, and selectively turning on a second proximity sensor. In some cases, the second proximity sensor may be a proximity sensor capable of detecting the proximity of the device to more distant objects, but at the cost of greater power consumption.

These and other techniques are described with reference to FIGS. 1-19. However, those skilled in the art will readily appreciate that the detailed description given herein with respect to these figures is for explanatory purposes only and should not be construed as limiting.

Directional terminology, such as "top", "bottom", "upper", "lower", "front", "back", "over", "under", "beneath", "left", "right", etc. may be used with reference to the orientation of some of the components in some of the figures described below. Because components in various embodiments can be positioned in a number of different orientations, directional terminology is used for purposes of illustration only and is in no way limiting. The directional terminology is intended to be construed broadly, and therefore should not be interpreted to preclude components being oriented in different ways. The use of alternative terminology, such as "or", is intended to indicate different combinations of the alternative elements. For example, A or B is intended to include, A, or B, or A and B.

FIG. 1 shows a functional block diagram of a device 100. In some examples, the device 100 may be a wearable device, such as an electronic watch, smart watch, health monitoring device, or fitness monitoring device that is wearable on a wrist. The device 100 may also or alternatively be wearable on an ankle, arm, forehead, waist, or other body part, or may be positionable or attachable to another device (e.g., a seat). The device 100 may include one or more input devices 102, one or more output devices 104, and a processor 106 (which processor may be a singular processor, a set of multiple processors, and/or a processor in combination with supporting circuitry). Broadly, the input device(s) 102 may detect various types of inputs or sense various types of parameters, and the output device(s) 104 may provide various types of outputs.

In some cases, inputs detected and/or parameters sensed by the input device(s) 102 may be used to control one or more settings, functions, or other aspects of the device 100. In some cases, one or more of the output devices 104 may be configured to provide outputs that are dependent on, or manipulated in response to, the inputs detected and/or parameters sensed by one one or more of the input devices 102. The outputs provided by one or more of the output devices 104 may also be responsive to, or initiated by, a program or application executed by the processor 106 and/or an associated companion device.

The processor 106 may receive input signals from the input device(s) 102, in response to inputs detected and/or parameters sensed by the input devices 102. The processor 106 may interpret the input signals. In response to the interpreted signals, the processor 106 may maintain or alter one or more settings, functions, or aspects of the device 100, and in some cases may transmit output signals to one or more of the output devices 104. In some cases, the processor 106 may transmit output signals to one or more of the output devices 104 independently of any input signal. The output signals may cause the output device(s) 104 to provide one or more outputs.

In various embodiments, the input device(s) 102 may include any suitable components for detecting inputs and/or sensing device, user, and/or environmental parameters. Examples of input devices 102 include audio sensors (e.g., microphones), optical or visual sensors (e.g., cameras and/or other electromagnetic radiation sensors (e.g., visible light or IR photodetectors), proximity sensors, touch sensors, force sensors, pressure sensors, mechanical devices (e.g., crowns, switches, buttons, or keys), vibration sensors, thermal sensors, self-mixing interferometry sensors, orientation sensors, motion sensors (e.g., accelerometers or velocity sensors), location sensors (e.g., global positioning system (GPS) devices), magnetic sensors, communication devices (e.g., wired or wireless communication devices), electroactive polymers (EAPs), resistive sensors, strain gauges, capacitive sensors, electrodes, and so on, or some combination thereof. Each input device 102 may be configured to detect one or more particular types of input and provide one or more signals (e.g., input signals) corresponding to the detected input(s) and/or sensed parameter(s). The signal(s) may be provided, for example, to the processor 106.

The output devices 104 may include any suitable components for providing outputs. Examples of output devices 104 include audio output devices (e.g., speakers), visual output devices (e.g., lights, displays, or other electromagnetic radiation emitters), tactile output devices (e.g., haptic output devices), communication devices (e.g., wired or wireless communication devices), and so on, or some combination thereof. Each output device 104 may be configured to receive one or more signals (e.g., output signals provided by the processor 106) and provide an output corresponding to the signal.

The processor 106 may be operably coupled to the input devices 102 and the output devices 104. The processor 106 may be adapted to exchange signals with the input devices 102 and the output devices 104. For example, the processor 106 may receive an input signal from an input device 102 that corresponds to an input detected by the input device 102. The processor 106 may interpret the received input signal to determine whether to provide and/or change one or more outputs in response to the input signal. The processor 106 may then send an output signal to one or more of the output devices 104, to provide and/or change outputs as appropriate. Examples of suitable processors are discussed in more detail below with respect to FIG. 17.

In some examples, the output devices 104 may include one or more electromagnetic radiation emitters, and the input devices 102 may include one or more photodetectors. At least two of the electromagnetic radiation emitters may emit beams of electromagnetic radiation having different IR wavelengths (e.g., at least a first IR wavelength and a second IR wavelength, but in some cases more than two IR wavelengths) into a matter detection space adjacent the device 100. The one or more photodetectors may be configured (e.g., filtered) to detect a set of wavelengths including the first IR wavelength and the second IR wavelength (and in some cases, more than two IR wavelengths). The processor 106 may be operated, at least in part, as a matter differentiation circuit (or as part of a matter differentiation circuit) to indicate, at least partly in response to signals generated by the one or more photodetectors that indicate amounts of the first IR wavelength and the second IR wavelength received by the one or more photodetectors, whether the device is likely proximate to human tissue.

In some examples, the input devices 102, or the input devices 102 in combination with the output devices 104, may include multiple proximity sensors. A first of the proximity sensors may be used to determine the proximity of the device 100 to an object, when possible, and a second of the proximity sensors may be selectively turned on when the proximity-sensing range of the first proximity sensor is exceeded (or, for example, when the second proximity sensor is more precise than the first proximity sensor and more precision is desired; or, for other reasons). In some cases, the second proximity sensor may be a proximity sensor capable of detecting the proximity of the device to more distant objects, but at the cost of greater power consumption.

Figure 2A:
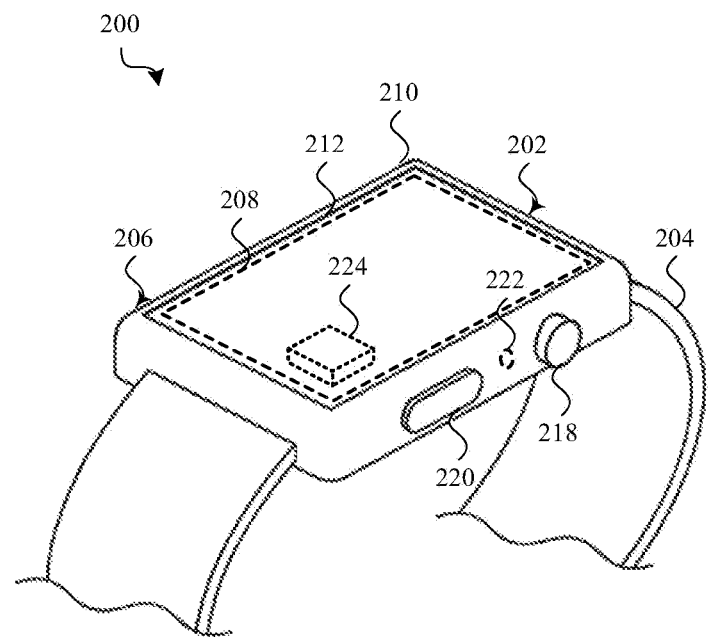
FIGS. 2A and 2B show an example of a device that includes a set of sensors.
Figure 2B:
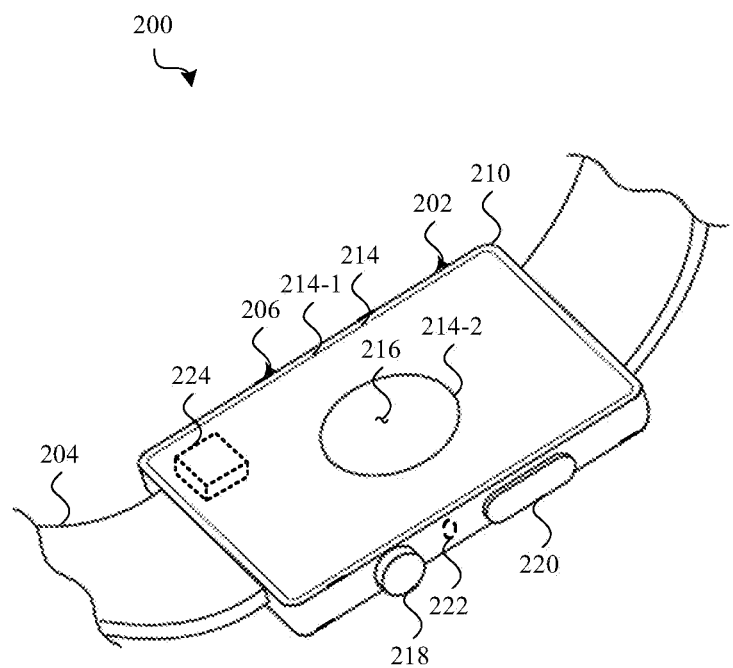

FIGS. 2A and 2B show an example of a device 200 that includes a set of sensors. The sensors may be used, for example, to determine whether the device 200 is likely proximate to human tissue, and/or to determine the proximity of the device 200 to an object (which object may in some cases be human tissue). The device's dimensions and form factor, and inclusion of a band 204 (e.g., a wrist band), suggest that the device 200 is an electronic watch. However, the device 200 could alternatively be any wearable electronic device. FIG. 2A shows a front isometric view of the device 200, and FIG. 2B shows a back isometric view of the device 200. The device 200 is an example of the device described with reference to FIG. 1.

The device 200 may include a body 202 (e.g., a watch body) and a band 204. The body 202 may include an input or selection device, such as a crown 218 or a button 220. The band 204 may be attached to a housing 206 of the body 202, and may be used to attach the body 202 to a body part (e.g., an arm, wrist, leg, ankle, or waist) of a user. The body 202 may include a housing 206 that at least partially surrounds a display 208. In some embodiments, the housing 206 may include a sidewall 210, which sidewall 210 may support a front cover 212 (FIG. 2A) and/or a back cover 214 (FIG. 2B). The front cover 212 may be positioned over the display 208, and may provide a window through which the display 208 may be viewed. In some embodiments, the display 208 may be attached to (or abut) the sidewall 210 and/or the front cover 212. In alternative embodiments of the device 200, the display 208 may not be included and/or the housing 206 may have an alternative configuration.

The display 208 may include one or more light-emitting elements including, for example, light-emitting elements that define a light-emitting diode (LED) display, organic LED (OLED) display, liquid crystal display (LCD), electroluminescent (EL) display, or other type of display. In some embodiments, the display 208 may include, or be associated with, one or more touch and/or force sensors that are configured to detect a touch and/or a force applied to a surface of the front cover 212.

In some embodiments, the sidewall 210 of the housing 206 may be formed using one or more metals (e.g., aluminum or stainless steel), polymers (e.g., plastics), ceramics, or composites (e.g., carbon fiber). The front cover 212 may be formed, for example, using one or more of glass, a crystal (e.g., sapphire), or a transparent polymer (e.g., plastic) that enables a user to view the display 208 through the front cover 212. In some cases, a portion of the front cover 212 (e.g., a perimeter portion of the front cover 212) may be coated with an opaque ink to obscure components included within the housing 206. In some cases, all of the exterior components of the housing 206 may be formed from a transparent material, and components within the device 200 may or may not be obscured by an opaque ink or opaque structure within the housing 206.

The back cover 214 may be formed using the same material(s) that are used to form the sidewall 210 or the front cover 212. In some cases, the back cover 214 may be part of a monolithic element that also forms the sidewall 210. In other cases, and as shown, the back cover 214 may be a multi-part back cover, such as a back cover having a first back cover portion 214-1 attached to the sidewall 210 and a second back cover portion 214-2 attached to the first back cover portion 214-1. The second back cover portion 214-2 may in some cases have a circular perimeter and an arcuate exterior surface 216 (i.e., an exterior surface 216 having an arcuate profile).

The front cover 212, back cover 214, or first back cover portion 214-1 may be mounted to the sidewall 210 using fasteners, adhesives, seals, gaskets, or other components. The second back cover portion 214-2, when present, may be mounted to the first back cover portion 214-1 using fasteners, adhesives, seals, gaskets, or other components.

A display stack or device stack (hereafter referred to as a "stack") including the display 208 may be attached (or abutted) to an interior surface of the front cover 212 and extend into an interior volume of the device 200. In some cases, the stack may include a touch sensor (e.g., a grid of capacitive, resistive, strain-based, ultrasonic, or other type of touch sensing elements), or other layers of optical, mechanical, electrical, or other types of components. In some cases, the touch sensor (or part of a touch sensor system) may be configured to detect a touch applied to an outer surface of the front cover 212 (e.g., to a display surface of the device 200).

In some cases, a force sensor (or part of a force sensor system) may be positioned within the interior volume below and/or to the side of the display 208 (and in some cases within the device stack). The force sensor (or force sensor system) may be triggered in response to the touch sensor detecting one or more touches on the front cover 212 (or a location or locations of one or more touches on the front cover 212), and may determine an amount of force associated with each touch, or an amount of force associated with the collection of touches as a whole. The force sensor (or force sensor system) may alternatively trigger operation of the touch sensor (or touch sensor system), or may be used independently of the touch sensor (or touch sensor system).

The device 200 may include various sensor systems (e.g., input devices, or input devices in combination with output devices), and in some embodiments may include some or all of the sensor systems included in the device described with reference to FIG. 1. In some embodiments, the device 200 may have a port 222 (or set of ports) on a side of the housing 206 (or elsewhere), and an ambient pressure sensor, ambient temperature sensor, internal/external differential pressure sensor, gas sensor, particulate matter concentration sensor, or air quality sensor may be positioned in or near the port(s) 222.

In some cases, one or more skin-facing sensors may be included within the device 200. The skin-facing sensor(s) may emit or transmit signals through the back cover 214 and/or receive signals or sense conditions through the back cover 214. For example, in some embodiments, one or more such sensors may include a number of electromagnetic radiation emitters (e.g., visible light and/or IR emitters), and/or a number of proximity sensors (e.g., capacitive, resistive, optical, self-mixing interference (SMI), or other types of proximity sensors). The sensors may be used, for example, to determine whether the back of the housing 206 (e.g., the back cover 214 or the second back cover portion 214-2) is likely proximate to human tissue, and/or to determine the proximity of the device 200 to an object. The sensors may also or alternatively be used as a device on/off wrist detector, a biometric sensor, a heart-rate monitor, a respiration-rate monitor, a blood pressure monitor, a blood oxygenation monitor, and/or a blood glucose monitor.

The device 200 may include circuitry 224 (e.g., a processor and/or other components) configured to compute or extract, at least partly in response to signals received directly or indirectly from one or more of the device's sensors, an indication of whether the back of the housing 206 (e.g., the back cover 214 or the second back cover portion 214-2) is likely proximate to human tissue. The circuitry 224 may also or alternatively be configured to determine the proximity of the device 200 to an object. Still further, the circuitry 224 may in some cases transition various of the device's sensors to an on state or an off state (e.g., a completely off state or a low power (or power conserving) state). In some embodiments, the circuitry 224 may convey the indication of whether the back of the housing 206 is likely proximate to human tissue, or an indication of the device's proximity to an object, via an output device of the device 200. For example, the circuitry 224 may cause the indication(s) to be displayed on the display 208, indicated via audio or haptic outputs, transmitted via a wireless communications interface or other communications interface, and so on. The circuitry 224 may also or alternatively maintain or alter one or more settings, functions, or aspects of the device 200, including, in some cases, what is displayed on the display 208.

Figure 3A:
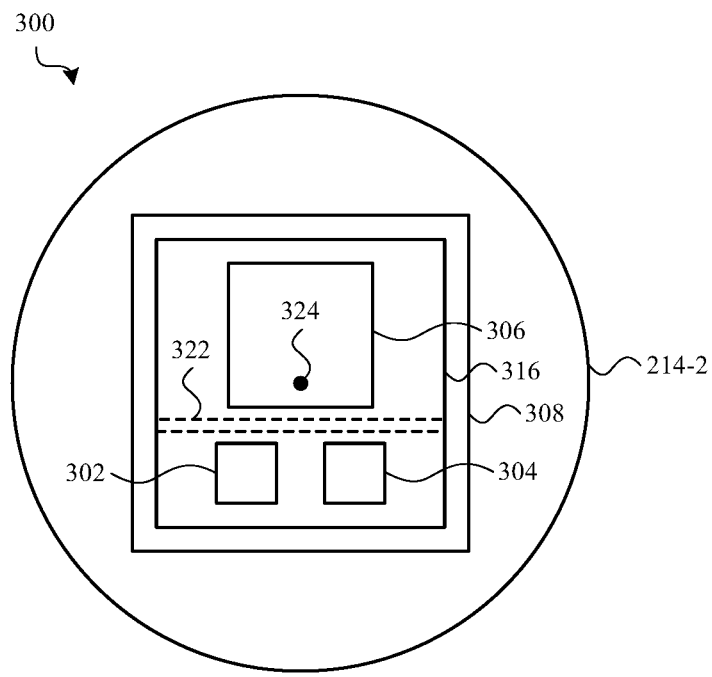
FIGS. 3A and 3B show an example of a skin-facing sensor (or sensor system) that may be included in the device described with reference to FIG. 1 or 2A-2B.
Figure 3B:
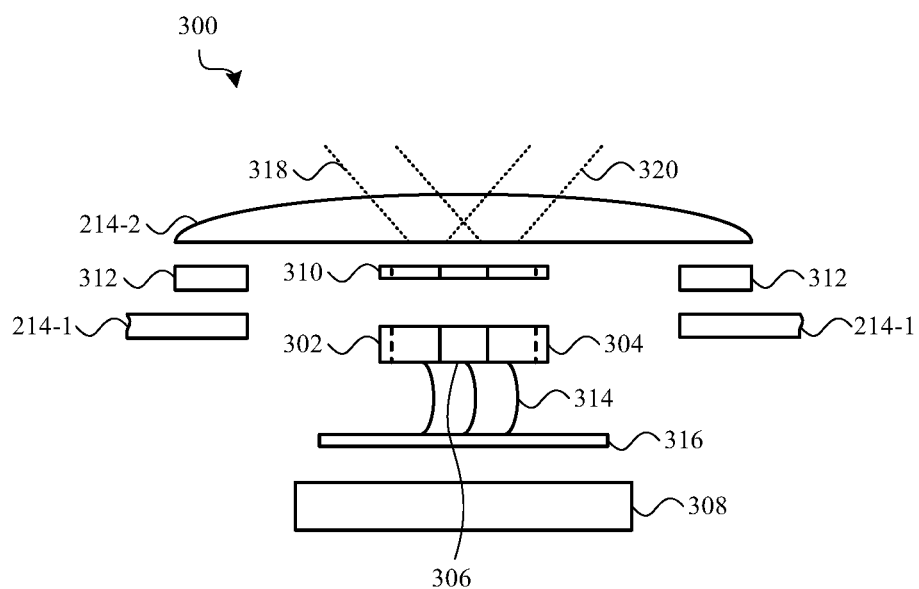

FIGS. 3A and 3B show an example of a skin-facing sensor (or sensor system 300) that may be included in the device described with reference to FIG. 1 or 2A-2B. By way of example, the sensor system 300 is shown to be positioned under a back or back cover of a housing (e.g., under the second back cover portion 214-2 described with reference to FIG. 2B). FIG. 3A shows a plan view of the sensor system 300, and FIG. 3B shows an elevation of the sensor system 300.

By way of example, and as shown in FIG. 3A, the sensor system 300 may include first and second emitters 302, 304 (electromagnetic radiation emitters) and a photodetector 306. By way of example, each of the emitters 302, 304 may include a vertical-cavity surface-emitting laser (VCSEL), a vertical external-cavity surface-emitting laser (VECSEL), a quantum-dot laser (QDL), a quantum cascade laser (QCL), a light-emitting diode (LED) (e.g., an organic LED (OLED), a resonant-cavity LED (RC-LED), a micro LED (mLED), a superluminescent LED (SLED), or an edge-emitting LED), or another type of light-emitting element. The first emitter 302 may be positioned within the housing described with reference to FIG. 1 or 2A-2B, and may be configured to emit a first beam of electromagnetic radiation through a back of the housing (e.g., through the second back cover portion 214-2). The first beam may have a first IR wavelength (or range of wavelengths including the first IR wavelength). The second emitter 304 may also be positioned within the housing, and may be configured to emit a second beam of electromagnetic radiation through the back of the housing (e.g., through the second back cover portion 214-2). The second beam may have a second IR wavelength (or range of wavelengths including the second IR wavelength). The second IR wavelength is different from the first IR wavelength. As will be described in greater detail with reference to FIG. 5, the first IR wavelength may have a first human tissue reflectance factor, and the second IR wavelength may have a second human tissue reflectance factor, with the first and second human tissue reflectance factors being different. In some embodiments, the sensor system 300 may include additional emitters, emitting the same or different wavelengths of electromagnetic radiation as the first and second emitters 302, 304.

The photodetector 306 may also be positioned within the housing, and may receive and detect reflections or backscatters of the first beam and the second beam (and/or additional beams, when additional emitters are used). In some embodiments, the photodetector 306 may be an Indium Gallium Arsenide (InGaAs) photodetector. In some cases, the photodetector 306 may be filtered to detect a set of electromagnetic radiation wavelengths including the first IR wavelength and the second IR wavelength. In some cases, the photodetector 306 may be filtered to detect a single range of electromagnetic radiation wavelengths. In other cases, the photodetector 306 may be filtered to detect the first IR wavelength or a first notch of IR wavelengths including the first IR wavelength, and filtered to detect the second IR wavelength or a second notch of IR wavelengths including the second IR wavelength. The photodetector 306 may be filtered, for example, by one or more coatings applied to the photodetector 306, by one or more optical filter elements disposed over the photodetector 306, or by a coating (e.g., an ink) applied to an interior or exterior surface of the second back cover portion 214-2. The first and/or second emitters 302, 304 may also be filtered, in the same way or in a different way as the photodetector 306. For example, if an emitter emits electromagnetic radiation that is outside a desired or useful range of wavelengths usable for matter differentiation, the electromagnetic radiation emitted by the emitter may be filtered to thereby limit the range of wavelengths that ultimately illuminate an object. The first and/or second emitter 302, 304 may be filtered, for example, by one or more coatings applied to an aperture of the first or second emitter 302, 304, by one or more optical filter elements disposed over an aperture of the first or second emitter 302, 304, or by a coating (e.g., an ink) applied to an interior or exterior surface of the second back cover portion 214-2. In various embodiments, one or all of the first emitter 302, the second emitter, or the photodetector 306 may be filtered.

Optionally, a set of one or more IR wavelength-blocking walls may be disposed between the photodetector 306 and emitters 302, 304. By way of example, a singular wall 322 is shown positioned between the photodetector 306 and emitters 302, 304 in FIG. 3A (but not in FIG. 3B). The wall 322 may extend from a substrate, to which the photodetector 306 and emitters 302, 304 are attached, to an interior surface of the second back cover portion 214-2. Alternatively, the wall 322 may extend further around, or entirely around, the photodetector 306; or further around, or entirely around, the emitters 302, 304; or further around, or entirely around, each emitter 302, 304 separately; or further around, or entirely around, each of the photodetector 306, the first emitter 302, and the second emitter 304. In some embodiments, one or more of the walls may extend into or through the second back cover portion 214-2. The wall(s), such as wall 322, may be used to reduce the likelihood that electromagnetic radiation emitted by one or both of the emitters 302, 304 will impinge on the photodetector 306 before entering and/or exiting the second back cover portion 214-2.

In some embodiments, and as shown, a group of sensing components including the first and second emitters 302, 304 and photodetector 306 may be positioned on-axis with respect to a center axis 324 of a back cover of a device (e.g., a center axis 324 of the second back cover portion 214-2), or the group of sensing components may be disposed around the center axis 324. The center axis 324 is perpendicular to the exterior surface of the back cover.

At least the photodetector 306, and in some cases the first and second emitters 302, 304, may be directly or indirectly connected to circuitry 308 (e.g., a processor (e.g., a general purpose processor programmed by suitable machine-readable instructions or software)) and/or other circuitry, which in some cases may include the processor described with reference to FIG. 1 or 2A-2B) that includes, or is configured to operate as, a timing circuit. The timing circuit may be configured to operate the first emitter 302 and the second emitter 304. In some embodiments, the first emitter 302 and second emitter 304 may be operated to respectively emit the first beam of electromagnetic radiation or the second beam of electromagnetic radiation at different times (e.g., sequentially). The timing circuit may be configured to operate the photodetector 306 to cause the photodetector 306 to integrate a charge indicative of 1) a first amount of electromagnetic radiation received by the photodetector 306 after the first emitter 302 emits the first beam, and 2) a second amount of electromagnetic radiation received by the photodetector 306 after the second emitter 304 emits the second beam.

The circuitry 308 may also include, or be configured to operate as, a matter differentiation circuit. The matter differentiation circuit may be configured to indicate, at least partly in response to signals indicating amounts of the first IR wavelength and the second IR wavelength received by the photodetector 306 (e.g., signals indicative of the integrated charges produced by reflections or backscatters of the respective first or second IR wavelengths), whether the back of the housing (e.g., the exterior surface of the second back cover portion 214-2) is likely proximate to human tissue.

In some cases, the indication of whether the back of the housing is likely proximate to human tissue may be based at least partly on a ratio of the first amount of electromagnetic radiation (i.e., the amount of the first IR wavelength) to the second amount of electromagnetic radiation (i.e., the amount of the second IR wavelength). For example, the matter differentiation circuit may determine a ratio of the first amount of electromagnetic radiation to the second amount of electromagnetic radiation, and compare the ratio to a threshold (or to a range). The matter differentiation circuit may then (only) indicate the back of the housing is likely proximate to human tissue when the ratio satisfies the threshold (or is within the range).

In some cases, the indication of whether the back of the housing is likely proximate to human tissue may be based at least partly on a relationship between the first amount of electromagnetic radiation, the second amount of electromagnetic radiation, and a ratio of the first amount of electromagnetic radiation to the second amount of electromagnetic radiation. For example, the matter differentiation circuit may compare each of the first amount of electromagnetic radiation, the second amount of electromagnetic radiation, and the ratio of the first amount of electromagnetic radiation to the second amount of electromagnetic radiation to respective thresholds (or ranges), and then (only) indicate the back of the housing is likely proximate to human tissue when each of the amounts and ratio satisfy their respective thresholds (or are within their respective ranges).

In some cases, the indication of whether the back of the housing is likely proximate to human tissue may be based at least partly on a modeling of human tissue (e.g., a modeling of a collection of human tissue examples). The modeling may include, for example, a modeling of human tissue's reflectance, absorption, scattering, and so on for different wavelengths of electromagnetic radiation. The modeling may be performed for a cross-section of the population; for a cross-section of potential users; for users having different characteristics (e.g., more or less hair, tattoos, different colored skin, and so on); or for particular users. In these embodiments, amounts of electromagnetic radiation received by the photodetector 306, or by different photodetectors (e.g., the photodetectors described with reference to FIGS. 7B, 7C, and 8A-9B, or different numbers or arrangement of photodetectors) may be compared to model data, and a determination of whether the back of the housing is likely proximate to human tissue may be based at least in part on the comparison. In some embodiments, machine learning or other techniques may be used to adapt or calibrate a model of human tissue and/or models of other types of matter (e.g., wood, glass, cloth, and so on). The model (and comparisons, adaptations, calibrations, and so on) may be multispectral.

In some cases, the indication of whether the back of the housing is likely proximate to human tissue may be based at least partly on a detected proximity (or distance) of an object. For example, the sensor system 300 may further include a proximity sensor (or distance sensor) 326 that is configured to detects a proximity (or distance) of an object to (or from) the back of the housing (e.g., to/from the second back cover portion 214-2). The sensed proximity or distance may be used (e.g., by the circuitry 306 when operated as a matter differentiation circuit) to adjust one or more of the thresholds (or ranges) to which the first amount of electromagnetic radiation, the second amount of electromagnetic radiation, or the ratio of the first amount of electromagnetic radiation to the second amount of electromagnetic radiation is/are compared. The proximity sensor (or distance sensor) 326 may be a capacitive, optical, self-mixing interference (SMI), ultrasonic, or other type of proximity or distance sensor.

In some cases, matter differentiation may be used to determine, for example, whether a device is being worn or is in a pocket, or is being worn or resting on a table or charging mat. Matter differentiation may also be used, in combination with accelerometer measurements obtained by a device, whether a user of the device is falling or whether the device is falling independent of the user. Matter differentiation may also be used to prevent health or fitness related data from being collected when a device is not proximate human tissue and is likely not being worn (or when the device is not proximate human tissue and its health or fitness-related sensors are unlikely to produce useful information because they are not proximate, or sufficiently proximate, human tissue). In some embodiments, the circuitry 308 may alert a user when their device is not sufficiently proximate their skin, and a sensor is unable to obtain useful health or fitness data.

In some cases, the matter differentiation circuit may always be active, or may be activated periodically. In other cases, the matter differentiation circuit may be activated by particular device functions or applications. For example a financial transaction application may activate the matter differentiation circuit to verify that a device is proximate human tissue before engaging in other password or biometric verifications.

The electromagnetic radiation-emitting apertures of the emitters 302, 304 may be equidistant from a centroid of the photodetector 306 as shown. Alternatively, the apertures of the emitters 302, 304 may be positioned different distances from a centroid of the photodetector 306. In some embodiments, the emitters 302, 304 may emit beams of electromagnetic radiation having the same size (e.g., same size cross-sections or spread from a plane of emission) and/or same optical power. In some embodiments, the emitters 302, 304 may emit beams of electromagnetic radiation having different sizes and/or different optical powers. By way of example, the emitters 302, 304 are shown to occupy surface areas that are equal size and smaller than a surface area occupied by the photodetector 306. However, the emitters 302, 304 may occupy the same or different size surface areas, and may occupy surface areas that are smaller, the same, or larger than the surface area occupied by the photodetector 306. The parameters of the emitters 302, 304 and photodetector 306 discussed in this paragraph, and/or other parameters of the emitters 302, 304 and photodetector 306, may be configured or adjusted in various ways to improve the matter differentiation circuit's ability to differentiate human tissue from other types of matter (or from particular types of matter). In some cases, an improvement in matter differentiation may be achieved by changing parameters of the emitters 302, 304 or photodetector 306 that tend to change the ratio of an amount of electromagnetic radiation including the first IR wavelength received by the photodetector 306, and an amount of electromagnetic radiation including the second IR wavelength received by the photodetector 306.

In some embodiments, the circuitry 308 may also include, or be configured to operate as, a power conservation circuit. For example, the circuitry 308 may be configured to reduce power supplied to a component of a device by a power source, or halt, delay, or alter a processing, communication, or sensing function of the device, when the matter differentiation circuit indicates the device is not likely proximate to human tissue.

As shown in the exploded view of FIG. 3B, the first and second emitters 302, 304 and photodetector 306 may be attached to an interior surface of the second back cover portion 214-2 using an adhesive 310. The emitters 302, 304 and photodetector 306 may be attached to the interior surface of the second back cover portion 214-2 apart from other components of a device housing. In some embodiments, the emitters 302, 304 and photodetector 306 may be attached directly to the interior surface (or to a lens or light control film or coating positioned between the interior surface and one or more of the emitters 302, 304 or photodetector 306), or one or more modules including the emitters 302, 304 and photodetector 306 may be attached directly to the interior surface (or to a lens or light control film or coating positioned between the interior surface and one or more of the emitters 302, 304 or photodetector 306). Alternatively, the emitters 302, 304 and/or photodetector 306 may be attached to a substrate or module that is attached directly to the interior surface of the second back cover portion 214-2 (or to a lens or light control film or coating positioned between the interior surface and the substrate or module). The second back cover portion 214-2 may similarly be attached to the first back cover portion 214-1 using an adhesive 312. The adhesives 310, 312 may be the same or different. The adhesive 312 may in some cases be a ring of adhesive disposed around the perimeter of the second back cover portion 214-2. The first and second emitters 302, 304 and photodetector 306 may be electrically connected to the circuitry 308 (e.g., an integrated circuit (IC) or printed circuit board (PCB)). In some cases, the first and second emitters 302, 304 and/or photodetector 306 may be electrically connected to the circuitry 308 via a set of fly wires 314 and/or a flex circuit 316.

The first and second emitters 302, 304 may emit electromagnetic radiation through the second back cover portion 214-1 in various spot or flood illumination patterns, and in some cases may emit electromagnetic radiation into substantially overlapping elliptical cones 318, 320.

In some embodiments, an IR transparent ink may be applied to the interior surface of the second back cover portion 214-2, in at least a region or regions disposed between the first and second emitters 302, 304 and photodetector 306, on one side, and the second back cover portion 214-2 on the other side. The IR transparent ink may in some cases block visible light or ambient light. In some embodiments, one or more lenses (e.g., one or more Fresnel lenses) or filters (e.g., one or more light control films (LCFs), linear variable filters (LVFs), bandpass (BP) filters, or polarizers) may also or alternatively be positioned between the first and second emitters 302, 304 and photodetector 306, on one side, and the second back cover portion 214-2 on the other side.

Figure 4A:
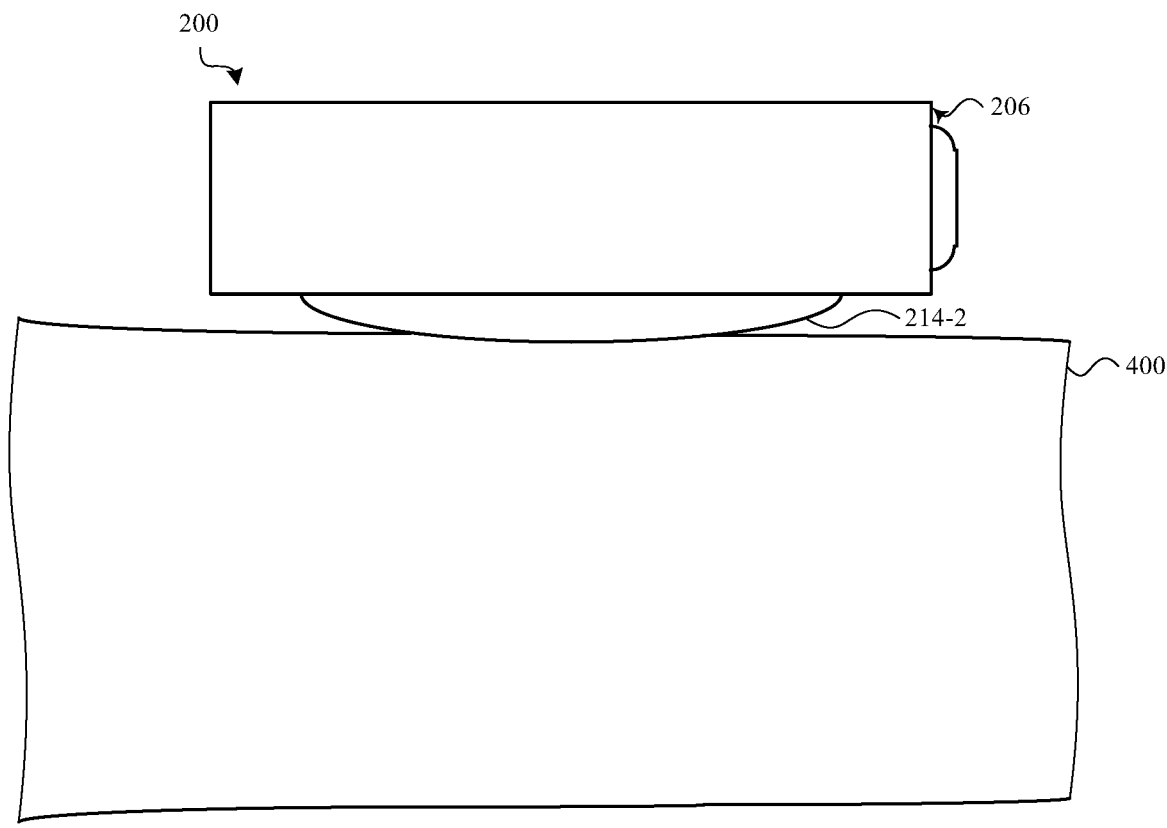
FIG. 4A shows the device described with reference to FIGS. 2A-2B when worn on a user's wrist, with the back cover of the device positioned against the user's wrist.
Figure 4B:
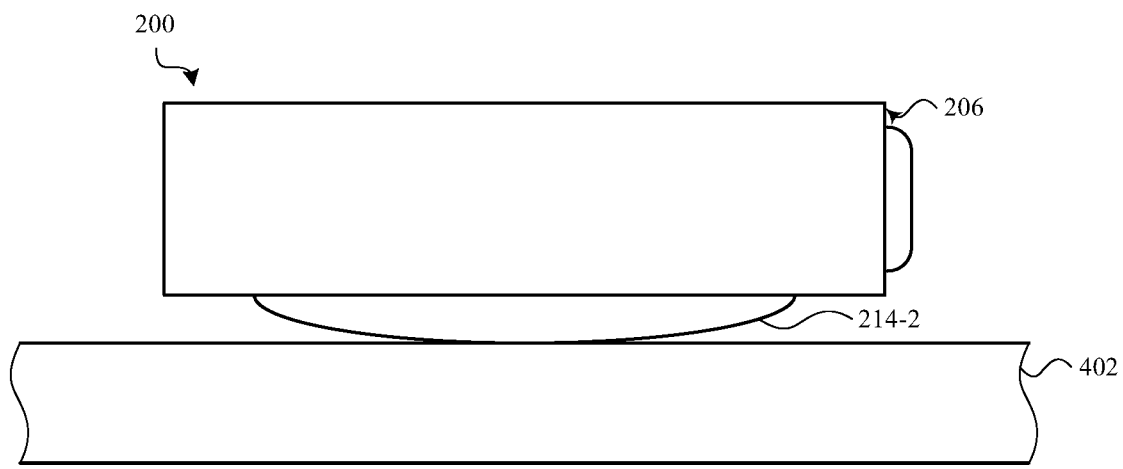
FIG. 4B shows the device described with reference to FIGS. 2A-2B when sitting on a table.

FIG. 4A shows the device 200 described with reference to FIGS. 2A-2B when worn on a user's wrist 400, with the back cover 214-2 of the device 200 positioned against the user's wrist 400 (i.e., human tissue). FIG. 4B shows the device 200 when sitting on a table 402. When the sensor system described with reference to FIGS. 3A-3B is included in the device 200, the matter differentiation circuit of the sensor system may operate the emitters and photodetector of the sensor system and indicate whether the back of the housing 206 (e.g., the second back cover portion 214-2) is likely proximate to human tissue, as shown in FIG. 4A, or likely proximate to an object that is not human tissue, as shown in FIG. 4B. An example basis for the matter differentiation circuit making its indication is described with reference to FIGS. 5 and 6.

In the scenario shown in FIG. 4A, electromagnetic radiation emitted by the emitters of the sensor system may propagate into the tissue of the user's wrist 400 and be absorbed into, or reflected or backscattered from, various structures within the user's wrist 400, including, for example, blood, water, lipids, skin, ligaments, tendons, and bone. Some of the electromagnetic radiation may be reflected or backscattered and received/detected by the photodetector of the sensor system. In the scenario shown in FIG. 4B, relatively little of the electromagnetic radiation emitted by the emitters of the sensor system may propagate into the table 402, and most of the electromagnetic radiation may reflect or backscatter from the surface of the table 402 and be received/detected by the photodetector of the sensor system.

Figure 5:
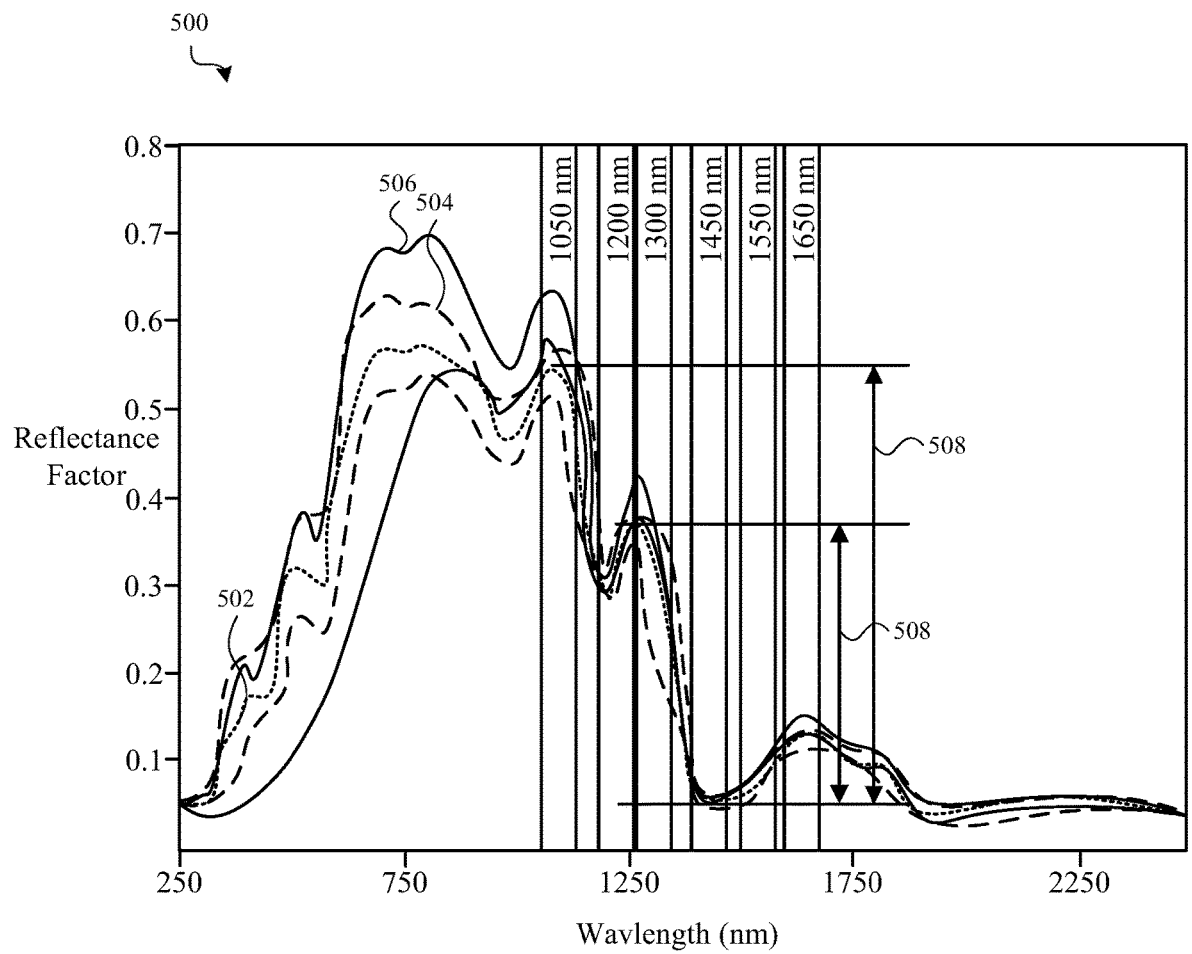
FIG. 5 shows an example graph of electromagnetic radiation wavelength versus human tissue reflectance factor.

FIG. 5 shows an example graph 500 of electromagnetic radiation wavelength (in nanometers (nm)) versus human tissue reflectance factor (a parameter without units). A reflectance factor may, in theory, range from a value of 0, indicating that an electromagnetic radiation wavelength is completely absorbed by an object, to a value of 1, indicating that an electromagnetic radiation wavelength is completely reflected by an object. FIG. 5 shows a mean human tissue reflectance factor 502 for each wavelength of electromagnetic radiation; a first sigma ($1\sigma$) spread of human tissue reflectance factors 504 for each wavelength of electromagnetic radiation (i.e., based on the variance of human tissue reflectance factor for different persons); and a range of human tissue reflectance factors 506 for each wavelength of electromagnetic radiation.

For human tissue, the reflectance factors for various wavelengths of electromagnetic radiation range from about 0.05 to about 0.70. In the IR range—and particularly in the near-infrared (NIR) band, ranging from 750-1400 nm, and the shorter end of the short-wavelength infrared (SWIR) band (e.g., from about 1400-2000 nm)—there is great variability in the human tissue reflectance factors of different IR wavelengths. This enables the selection of first and second IR wavelengths with significant contrast 508 between their human tissue reflectance factors. For example, there is contrast between 1450 nm, which is highly absorbed by human tissue, and 1300 nm, which has a human tissue reflectance factor about eight times (8×) that of 1450 nm. Even more contrast is provided between 1450 nm and 1050 nm, which has a human tissue reflectance factor about eleven times (11×) that of 1450 nm. Contrast is also provided, to different degrees, at other electromagnetic radiation wavelengths.

For objects other than human tissue on which a device such as the device described with reference to FIGS. 2A-2B may be placed (e.g., objects having wood, polymer (e.g., plastic), glass, and/or ceramic materials or surfaces), as shown in FIG. 4B, the object's reflectance factors for different wavelengths of electromagnetic radiation may have a much smaller variation. That is, the reflectance factors for different wavelengths of electromagnetic radiation may be spectrally flat or have little contrast.

In some embodiments of the sensor system described with reference to FIGS. 3A-3B, the first emitter 302 may be configured to emit a first IR wavelength of 1050 nm, 1200 nm, or 1300 nm, for example, and the second emitter 304 may be configured to emit a second IR wavelength of 1450 nm, 1550 nm, or 1650 nm, for example. In other embodiments, the first and second emitters 302, 304 may be configured to emit other wavelengths that are useful in differentiating matter (e.g., differentiating human skin from other matter). In some cases, the pair of IR wavelengths may be selected not only because their human tissue reflectance factors have high contrast, but because their reflectance factors for other objects have low contrast. When the first and second emitters 302, 304 sequentially emit electromagnetic radiation and the photodetector 306 is operated to detect a first amount of electromagnetic radiation received after the first emitter 302 emits the first IR wavelength, and a second amount of electromagnetic radiation received after the second emitter 304 emits the second IR wavelength, the matter differentiation circuit may indicate that the second back cover portion 214-2 is likely proximate to human tissue when a ratio of the first amount of electromagnetic radiation to the second amount of electromagnetic radiation satisfies a first threshold (or alternatively, is within a first range) associated with human tissue. When the ratio does not satisfy the first threshold (or alternatively, is not within the first range, or satisfies a second threshold, or is within a second range), the matter differentiation circuit may indicate that the second back cover portion 214-2 is likely not proximate to human tissue.

Figure 6:
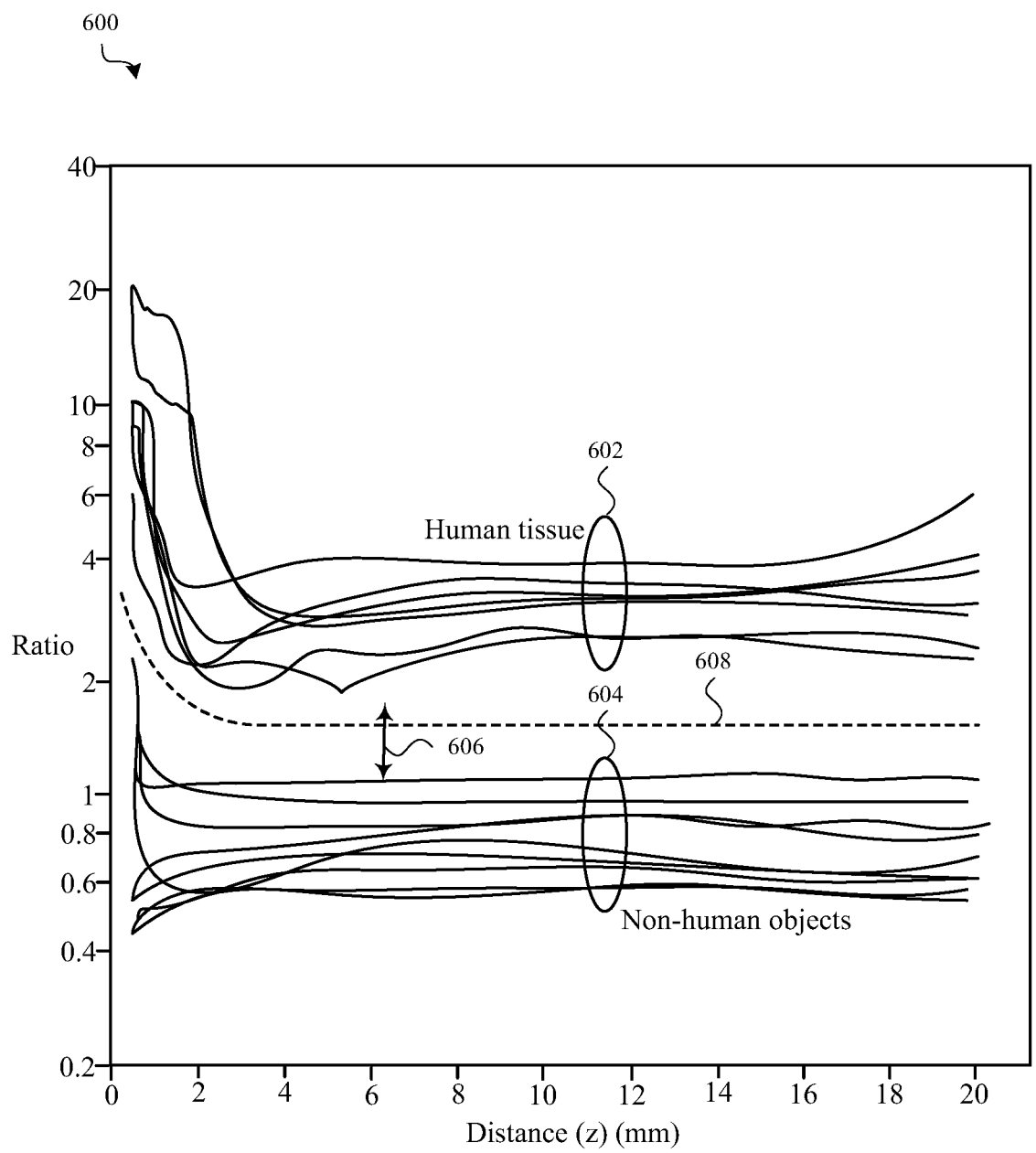
FIG. 6 shows an example distribution of the ratio discussed with reference to FIGS. 3A-3B and 5.

FIG. 6 shows an example distribution 600 of the ratio discussed with reference to FIGS. 3A-3B and 5. The distribution 600 is for human tissue and non-human objects located at various distances from a back cover or back of a device housing. By way of example, the ratio corresponds to an amount of a first IR wavelength at 1050 nm versus an amount of a second IR wavelength at 1450 nm.

As shown, the ratio is at or above about 1.9 for a variety of human tissue samples 602 (e.g., wrist tissue samples), which human tissue samples 602 are in a range of 0-20 millimeters (mm) from an exterior surface of a back cover. The ratio is generally about 1.0 for a variety of non-human object samples 604, which non-human object samples 604 are in a range of 1-20 mm from the exterior surface of the back cover. The ratio moves somewhat above 1.0 for a couple of the non-human object samples at close range (e.g., at a distance of about 1 mm or less), but still remains well below the ratio for human tissue at close range. The margin 606 between the ratio for human tissue and non-human objects is what enables ratio thresholds or ranges to be identified so that a matter differentiation circuit may indicate whether a back cover or back of a housing is likely proximate to human tissue. The indication is an indication of whether the back cover or back of the housing is "likely proximate" to human tissue because some objects may have reflectance factors, for different electromagnetic radiation wavelengths, that are similar to human tissue reflectance factors. For example, a wet and wadded cloth or paper towel may in some cases have reflectance factors that are similar to those of human tissue.

In some cases, a matter differentiation circuit may use the ratio discussed with reference to FIGS. 3A-3B, 5, and 6, in combination with other parameters, to indicate whether a back cover or back of a housing is likely proximate to human tissue. For example, the matter differentiation circuit may use the amounts of electromagnetic radiation that are used to compute the ratio separately, in addition to using the amounts in combination (e.g., to compute the ratio). In some cases, each amount of electromagnetic radiation may be separately compared to a threshold or expected range, and the matter differentiation circuit may indicate the back cover or back of the housing is likely proximate to human tissue when each parameter satisfies its respective threshold or is within its respective range.

In some cases, a matter differentiation circuit may analyze a change in ratio as an object approaches or moves farther away. For example, for two types of matter that have similar ratios, a distance-dependent variance (or lack of variance) in the ratio described with reference to FIG. 6 may be used to distinguish one type of matter (e.g., human tissue) from another (e.g., wood).

In some cases, a matter differentiation circuit may adjust a threshold (or thresholds) to which it compares a sensed amount of the first IR wavelength, a sensed amount of the second IR wavelength, or a ratio of a sensed amount of the first IR wavelength and a sensed amount of the second IR wavelength. For example, the matter differentiation circuit may adjust a threshold ratio 608 of the sensed amount of the first IR wavelength and a sensed amount of the second IR wavelength in response to a sensed proximity or distance of a back cover or back of a device housing to an object (e.g., a user's skin, a table top, and so on). As shown in the example of FIG. 6, when a proximity or distance sensor senses an object at a distance of about 2 mm or greater, the matter differentiation circuit may adjust the threshold ratio 608 to about 1.5 (or between about 1.2 and about 1.8). However, as the sensed distance to the object falls, and the object moves closer to the back cover or housing of the device, the matter differentiation circuit may adjust the threshold ratio 608 higher, to a value between about 3 or about 4 (or between about 1.2 and about 6). The particular value of the threshold ratio 608, and adjustments thereof, will sometimes depend on the configurations of the various sensors, including their size, placement, spacing, emission power, emission/detection wavelengths, and so on.

In some cases, the IR wavelengths of the first and second emitters described with reference to FIGS. 3A-3B may be selected or adjusted to improve the differentiation of particular materials or surfaces from human tissue.

FIGS. 7A-7D show various alternative plan views of a skin-facing sensor (or sensor system) that may be included in the device described with reference to FIG. 1, 2A-2B, or 4A-4B. Each of the sensor systems may be positioned under the second back cover portion 214-2 of the device described with reference to FIG. 2, or under a skin-facing housing or cover of any device, or under a back cover or back of a housing of any wearable device.

Figure 7A:
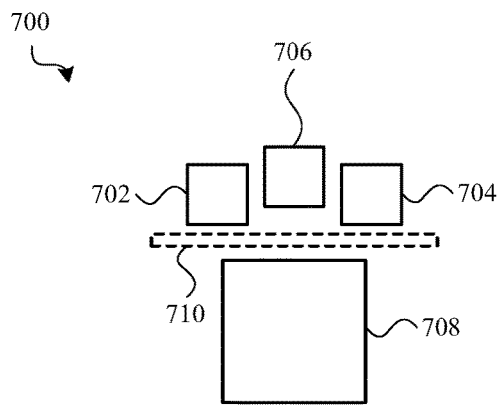
FIGS. 7A-7D show various alternative plan views of a skin-facing sensor (or sensor system) that may be included in the device described with reference to FIG. 1, 2A-2B, or 4A-4B.

The sensor system 700 shown in FIG. 7A includes three emitters (e.g., a first emitter 702, a second emitter 704, and a third emitter 706) and a photodetector 708. By way of example, the emitters 702, 704, 706 may include VCSELs, VECSELs, QDLs, QCLs, LEDs (e.g., OLEDs, RC-LEDs, mLEDs, SLEDs, or edge-emitting LEDs), or other types of light-emitting elements. At least two of the emitters may be IR emitters that emit beams of electromagnetic radiation having different IR wavelengths. The other emitter may be another IR emitter that emits a beam of electromagnetic radiation having the same IR wavelength as a beam of electromagnetic radiation emitted by another one of the emitters (e.g., to increase the optical power or improve the detectability of that wavelength). Alternatively, the other emitter may be another IR emitter that emits a beam of electromagnetic radiation having a different IR wavelength as the beams of electromagnetic radiation emitted by the other emitters (e.g., an IR wavelength that has the same or different reflectance factors, as the other emitted IR wavelengths, for human tissue and/or non-human objects). Alternatively, the other emitter may be a non-IR emitter (e.g., a visible light emitter) that emits a beam of electromagnetic radiation having a wavelength that has the same or different reflectance factors, as the emitted IR wavelengths, for human tissue and/or non-human objects. In some embodiments, a third emitter (or fourth emitter, and so on) may improve a matter differentiation circuit's ability to differentiate human tissue from a particular type or types of non-human objects. A third emitter (or fourth emitter, and so on) may also or alternatively enable the sensor system 700 to provide other kinds of sensing.

The emitters 702, 704, 706 may be positioned around the photodetector 708 and have electromagnetic radiation-emitting apertures that are equidistant from a centroid of the photodetector 708, as shown. Alternatively, the apertures of the emitters 702, 704, 706 may be positioned different distances from a centroid of the photodetector 708. In some embodiments, the emitters 702, 704, 706 may emit beams of electromagnetic radiation having the same size (e.g., same size cross-sections or spread from a plane of emission) and/or same optical power. In some embodiments, the emitters 702, 704, 706 may emit beams of electromagnetic radiation having different sizes and/or different optical powers. By way of example, the emitters 702, 704, 706 are shown to occupy surface areas that are equal size and smaller than a surface area occupied by the photodetector 708. However, the emitters 702, 704, 706 may occupy the same or different size surface areas, and may occupy surface areas that are smaller, the same, or larger than the surface area occupied by the photodetector 708. The parameters of the emitters 702, 704, 706 and photodetector 708 discussed in this paragraph, and/or other parameters of the emitters 702, 704, 706 and photodetector 708, may be configured or adjusted in various ways to improve a matter differentiation circuit's ability to differentiate human tissue from other types of matter (or from particular types of matter). In some cases, an improvement in matter differentiation may be achieved by changing parameters of the emitters 702, 704, 706 or photodetector 708 that tend to change the ratio of: an amount of electromagnetic radiation including the first IR wavelength received by the photodetector 708, and an amount of electromagnetic radiation including the second IR wavelength received by the photodetector 708.

The photodetector 708 may receive and detect reflections or backscatters of the first beam, the second beam, and the third beam. In some cases, the photodetector 708 may be filtered to detect a set of electromagnetic radiation wavelengths including a first IR wavelength emitted by the first emitter 702, a second IR wavelength emitted by the second emitter 704, and a third wavelength emitted by the third emitter 706. The first IR wavelength and second IR wavelength may be different, and the third wavelength may be the same as (or different from) each of the first and second IR wavelengths. In some embodiments, the photodetector 708 may be an InGaAs photodetector. In some cases, the photodetector 708 may be filtered to detect a single range of electromagnetic radiation wavelengths. In other cases, the photodetector 708 may be filtered to detect the first IR wavelength or a first notch of IR wavelengths including the first IR wavelength; filtered to detect the second IR wavelength or a second notch of IR wavelengths including the second IR wavelength; and/or filtered to detect the third wavelength or a first notch of wavelengths including the third wavelength. The photodetector 708 may be filtered, for example, by one or more coatings applied to the photodetector 708, by one or more optical filter elements disposed over the photodetector 708, or by a coating (e.g., an ink) applied to an interior or exterior surface of a cover or housing portion (e.g., the second back cover portion described with reference to FIG. 2B) through which the emitters 702, 704, 706 emit their beams of electromagnetic radiation.

Optionally, a set of one or more IR wavelength-blocking walls may be disposed between the photodetector 708 and emitters 702, 704, 706. By way of example, a singular wall 710 is shown positioned between the photodetector 708 and emitters 702, 704, 706 in FIG. 7A, but any number of walls may be used to reduce the likelihood that electromagnetic radiation emitted by one or more of the emitters 702, 704, 706 will impinge on the photodetector 708 before entering and/or exiting the second back cover portion 214-2. Examples of various additional or alternative wall configurations are described with reference to FIG. 3A.

At least the photodetector 708, and in some cases the emitters 702, 704, 706, may be directly or indirectly connected to circuitry (e.g., a processor (e.g., a general purpose processor programmed by suitable machine-readable instructions or software) and/or other circuitry, which in some cases may include the processor or circuitry described with reference to FIG. 1, 2A-2B, or 3A-3B) that includes, or is configured to operate as, a timing circuit and/or matter differentiation circuit, as described, for example, with reference to FIGS. 3A-3B. The matter differentiation circuit may be configured to indicate whether the back of the housing is likely proximate to human tissue at least partly in response to signals indicating detected amounts of the wavelengths of the first beam of electromagnetic radiation received by the photodetector 708, the second beam of electromagnetic radiation received by the photodetector 708, and/or the third beam of electromagnetic radiation received by the photodetector 708. For example, the matter differentiation circuit may be configured to indicate whether the back of the housing is likely proximate to human tissue at least partly in response to one or more of: a first signal indicating an amount of the first IR wavelength received by the photodetector 708, a second signal indicating an amount of the second IR wavelength received by the photodetector 708, or a third signal indicating an amount of the third wavelength received by the photodetector 708. The signals may in some cases be generated sequentially, after the timing circuit sequentially turns on, and then off, one of the emitters 702, 704, 706 at a time.

Figure 7B:
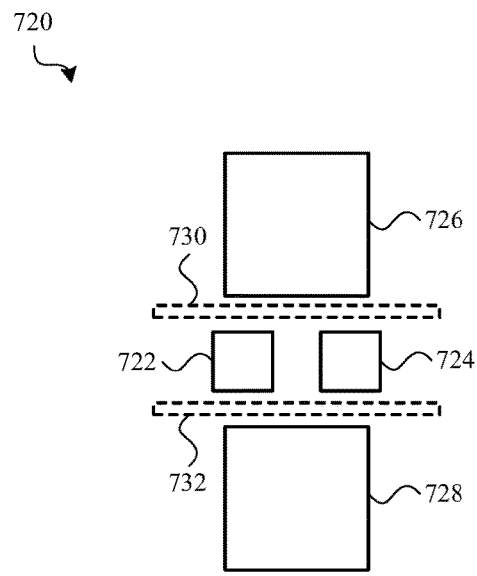

The sensor system 720 shown in FIG. 7B includes two emitters (e.g., a first emitter 722, and a second emitter 724) and two photodetectors 726, 728. By way of example, the emitters 722, 724 may include VCSELs, VECSELs, QDLs, QCLs, LEDs (e.g., OLEDs, RC-LEDs, mLEDs, SLEDs, or edge-emitting LEDs), or other types of light-emitting elements, and may be IR emitters that emit beams of electromagnetic radiation having different IR wavelengths.

The emitters 722, 724 may be positioned near and/or between the photodetectors 726, 728 and have electromagnetic radiation-emitting apertures that are equidistant from centroids of each of the photodetectors 726, 728, as shown. Alternatively, the apertures of the emitters 722, 724 may be positioned different distances from a centroid of a photodetector, or a single one (or both) of the emitters 722, 724 may have an electromagnetic radiation-emitting aperture that is positioned different distances from the centroids of the different photodetectors 726, 728. In some embodiments, the emitters 722, 724 may emit beams of electromagnetic radiation having the same size (e.g., same size cross-sections or spread from a plane of emission) and/or same optical power. In some embodiments, the emitters 722, 724 may emit beams of electromagnetic radiation having different sizes and/or different optical powers. By way of example, the emitters 722, 724 are shown to occupy surface areas that are equal size and smaller than surface areas occupied by the photodetectors 726, 728. However, the emitters 722, 724 may occupy the same or different size surface areas, and may occupy surface areas that are smaller, the same, or larger than the surface areas occupied by the photodetectors 726, 728. The photodetectors 726, 728 may also occupy different surface areas. The parameters of the emitters 722, 724 and photodetectors 726, 728 discussed in this paragraph, and/or other parameters of the emitters 722, 724 and photodetectors 726, 728, may be configured or adjusted in various ways to improve a matter differentiation circuit's ability to differentiate human tissue from other types of matter (or from particular types of matter). In some cases, an improvement in matter differentiation may be achieved by changing parameters of the emitters 722, 724 or photodetectors 726, 728 that tend to change the ratio of an amount of electromagnetic radiation including the first IR wavelength received by the photodetectors 726, 728, and an amount of electromagnetic radiation including the second IR wavelength received by the photodetectors 726, 728.

The photodetectors 726, 728 may receive and detect reflections or backscatters of the first beam and the second beam. In some cases, each of the photodetectors 726, 728 may be filtered to detect a set of electromagnetic radiation wavelengths including a first IR wavelength emitted by the first emitter 722, and a second IR wavelength emitted by the second emitter 724. The first IR wavelength and second IR wavelength may be different. In some embodiments, each photodetector 726, 728 may be an InGaAs photodetector. In some cases, each photodetector 726, 728 may be filtered to detect a single range of electromagnetic radiation wavelengths. In other cases, each photodetector 726, 728 may be filtered to detect the first IR wavelength or a first notch of IR wavelengths including the first IR wavelength, and filtered to detect the second IR wavelength or a second notch of IR wavelengths including the second IR wavelength. The photodetectors 726, 728 may be filtered, for example, by one or more coatings applied to the photodetectors 726, 728, by one or more optical filter elements disposed over the photodetectors 726, 728, or by a coating (e.g., an ink) applied to an interior or exterior surface of a cover or housing portion (e.g., the second back cover portion described with reference to FIG. 2B) through which the emitters 722, 724 emit their beams of electromagnetic radiation. In some cases, the photodetectors 726, 728 may be filtered differently. For example, the first photodetector 726 may be filtered to receive the first IR wavelength, and the second photodetector 728 may be filtered to receive the second IR wavelength.

Optionally, a set of one or more IR wavelength-blocking walls may be disposed between each photodetector 726, 728 and the emitters 722, 724. By way of example, a first wall 730 is shown positioned between the first photodetector 726 and the emitters 722, 724, and a second wall 732 is shown positioned between the second photodetector 728 and the emitters 722, 724. Alternatively, any number of walls may be used to reduce the likelihood that electromagnetic radiation emitted by one or both of the emitters 722, 724 will impinge on the first or second photodetector 726, 728 before entering and/or exiting a back cover of a device. Examples of various additional or alternative wall configurations are described with reference to FIG. 3A.

At least the photodetectors 726, 728, and in some cases the emitters 722, 724, may be directly or indirectly connected to circuitry (e.g., a processor (e.g., a general purpose processor programmed by suitable machine-readable instructions or software) and/or other circuitry, which in some cases may include the processor or circuitry described with reference to FIG. 1, 2A-2B, or 3A-3B) that includes, or is configured to operate as, a timing circuit and/or matter differentiation circuit, as described, for example, with reference to FIGS. 3A-3B. The matter differentiation circuit may be configured to indicate whether the back of the housing is likely proximate to human tissue at least partly in response to signals indicating detected amounts of the wavelengths of the first beam of electromagnetic radiation and/or the second beam of electromagnetic radiation received by the photodetectors 726, 728. For example, the matter differentiation circuit may be configured to indicate whether the back of the housing is likely proximate to human tissue at least partly in response to one or more of a first signal indicating an amount of the first IR wavelength received by the first photodetector 726, a second signal indicating an amount of the first IR wavelength received by the second photodetector 728, a third signal indicating an amount of the second IR wavelength received by the first photodetector 726, or a fourth signal indicating an amount of the second IR wavelength received by the second photodetector 728. The signals may in some cases be generated in pairs (e.g., one signal from each photodetector 726, 728), after the timing circuit sequentially turns on, and then off, one of the emitters 722, 724 at a time.

Figure 7C:
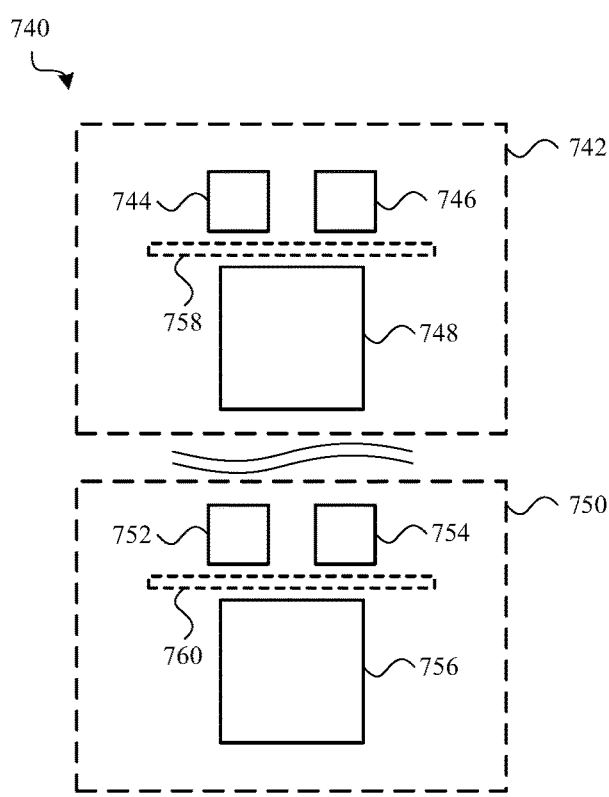

The sensor system 740 shown in FIG. 7C includes two groups of sensing components, with each group including two emitters and a photodetector (e.g., a first group 742 including a first emitter 744, a second emitter 746, and a first photodetector 748; and a second group 750 including a third emitter 752, a fourth emitter 754, and a second photodetector 756). By way of example, the emitters 744, 746, 752, 754 may include VCSELs, VECSELs, QDLs, QCLs, LEDs (e.g., OLEDs, RC-LEDs, mLEDs, SLEDs, or edge-emitting LEDs), or other types of light-emitting elements, and may be IR emitters that emit beams of electromagnetic radiation having different IR wavelengths. For example, the first and third IR emitters 744, 752 may be respectively configured to emit first and third beams of electromagnetic radiation having a first IR wavelength, and the second and fourth IR emitters 746, 754 may be respectively configured to emit second and fourth beams of electromagnetic radiation having a second IR wavelength. In this manner a beam having the first IR wavelength and a beam having the second IR wavelength is emitted by each group 742, 750 of sensing components. The emitters and photodetectors of each group 742, 750 may otherwise be configured and positioned as described with reference to any of FIG. 3A-3B, 7A, or 7B, and a set of one or more IR wavelength-blocking walls 758, 760 may optionally be disposed between each photodetector 748, 756 and the emitters 744, 746, 752, 754, as described, for example, with reference to any of FIG. 3A, 7A, or 7B. However, in contrast to a group of sensing components being positioned on-axis with respect to a center axis of a back cover, or being distributed around the center axis, the groups 742, 750 of sensing components shown in FIG. 7C may be distributed around a center axis of a back cover. In some cases, each sensing component within a group 742, 750 may be positioned off-axis with respect to the center axis (e.g., generally to one side of, or within one range of angular extents about, the center axis).

At least the photodetectors 748, 756, and in some cases the emitters 744, 746, 752, 754, may be directly or indirectly connected to circuitry (e.g., a processor (e.g., a general purpose processor programmed by suitable machine-readable instructions or software) and/or other circuitry, which in some cases may include the processor or circuitry described with reference to FIG. 1, 2A-2B, or 3A-3B) that includes, or is configured to operate as, a timing circuit and/or matter differentiation circuit, as described, for example, with reference to FIGS. 3A-3B. The matter differentiation circuit may be configured to indicate whether the back of the housing is likely proximate to human tissue at least partly in response to signals indicating detected amounts of the wavelengths of the first beam of electromagnetic radiation and/or the second beam of electromagnetic radiation received by the photodetectors 748, 756. In some embodiments, the matter differentiation may select whether to use signals generated by one or the other or both of the photodetectors 748, 756 when indicating whether the back of the housing is likely proximate to human tissue. In some cases, the matter differentiation circuit may determine which signals to use based, at least in part, on the strengths of the signals, the strengths of a subset of the signals, whether the signals satisfy particular thresholds or are within particular ranges, or signals generated by on/off wrist sensors, device tilt sensors, or device orientation sensors.

Figure 7D:
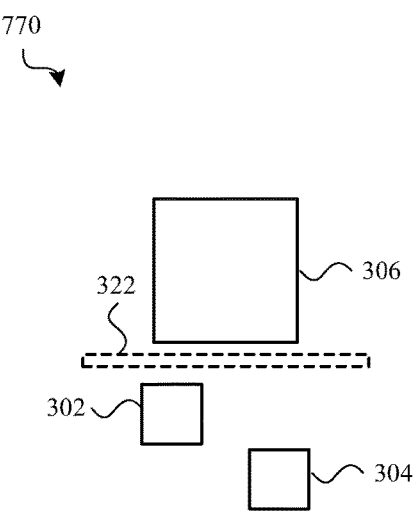

The sensor system 770 shown in FIG. 7D includes two emitters (e.g., a first emitter 302, and a second emitter 304) and a photodetector 306, similarly to the sensor system described with reference to FIGS. 3A and 3B. By way of example, the emitters 302, 304 may include VCSELs, VECSELs, QDLs, QCLs, LEDs (e.g., OLEDs, RC-LEDs, mLEDs, SLEDs, or edge-emitting LEDs), or other types of light-emitting elements, and may be IR emitters that emit beams of electromagnetic radiation having different IR wavelengths.

The emitters 302, 304 and photodetector 306 may be configured as described with reference to FIGS. 3A and 3B, and may be separated by a set of one or more IR wavelength-blocking walls, such as wall 322. However, in contrast to the sensor system described with reference to FIGS. 3A and 3B, the apertures of the emitters 302, 304 are positioned different distances from a centroid of the photodetector 306 (e.g., the aperture of the emitter 302 is closer to the centroid of the photodetector 306 than the aperture of the emitter 304). The emitters 302, 304 may be offset or staggered with respect to the photodetector 306 in various alternative ways. For example, and in some cases (not shown), the centroids of the emitters 302, 304 and photodetector 306 may be aligned, with the emitter 302 being positioned between the emitter 304 and the photodetector 306. Also or alternatively, and in some embodiments, the sizes or optical powers of the beams emitted by the emitters 302, 304 may be varied with respect to each other, or other parameters of the emitters 302, 304 may be varied, to improve a matter differentiation circuit's ability to differentiate human tissue from other types of matter (or from particular types of matter). In some cases, an improvement in matter differentiation may be achieved by changing parameters of the emitters 302, 304 that tend to change the ratio of an amount of electromagnetic radiation including the first IR wavelength received by the photodetector 306 to an amount of electromagnetic radiation including the second IR wavelength received by the photodetector 306. In some cases, varying the parameters or configurations of the emitters 302, 304 may make a human tissue or non-human object ratio curve flatter with variations in distance, or raise a human tissue ratio curve, or lower a non-human object ratio curve. All of these changes can increase the margin between human tissue ratio curves and non-human object ratio curves. Variations in emitter parameters may be especially useful in lowering the ratio of received/reflected IR wavelengths for non-human objects, at or around the point of contact between an object and a device (especially in the case of non-human objects with some amount of volume scattering).

Figure 8A:
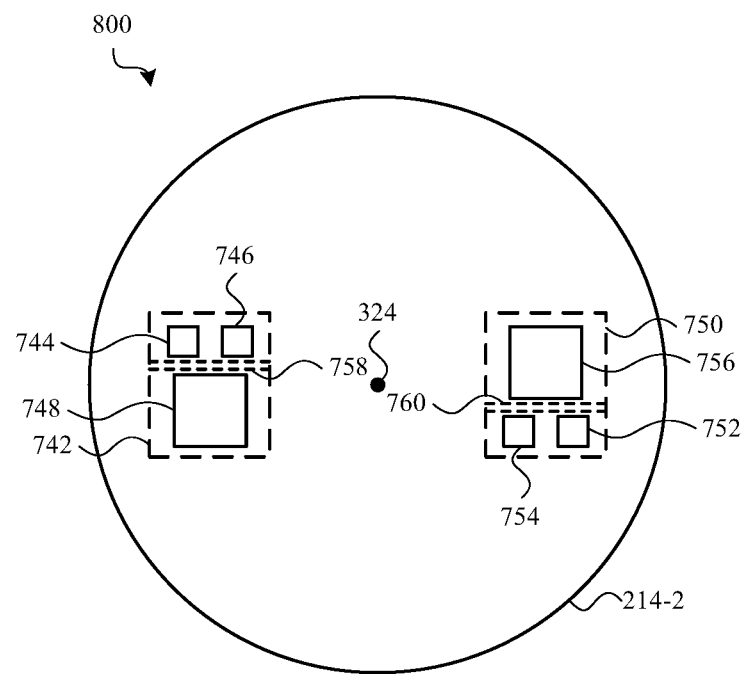
FIGS. 8A and 8B show an example of a skin-facing sensor (or sensor system) that may be included in the device described with reference to FIG. 1, 2A-2B, or 4A-4B.
Figure 8B:
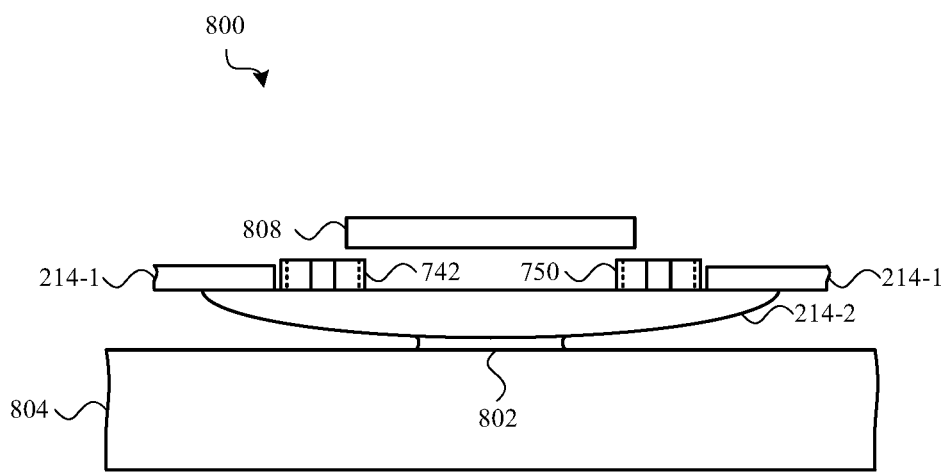

FIGS. 8A and 8B show an example of a skin-facing sensor (or sensor system 800) that may be included in the device described with reference to FIG. 1, 2A-2B, or 4A-4B. By way of example, the sensor system 800 is shown to be positioned under a back or back cover of a housing (e.g., under the second back cover portion 214-2 described with reference to FIG. 2B). FIG. 8A shows a plan view of the sensor system 800, and FIG. 8B shows an elevation of the sensor system 800.

The sensor system 800 includes the groups 742, 750 of sensing components described with reference to FIG. 7C, but the groups 742, 750 of sensing components are positioned differently with respect to each other than what is shown in FIG. 7C. In particular, the sensing components of the groups 742, 750 are positioned on opposite sides of a center axis 324 of the second back cover portion 214-2 (e.g., the groups 742, 750 are positioned off-axis with respect to the center axis 324), and are rotated 180 degrees with respect to each other along a diameter of the second back cover portion 214-2.

As shown in the elevation of FIG. 8B, the first and second groups 742, 750 of sensing components may be attached to an interior surface of the second back cover portion 214-2 using an adhesive. The groups 742, 750 of sensing components may be attached to the interior surface of the second back cover portion 214-2 apart from other components of a device housing. In some embodiments, the groups 742, 750 of sensing components may be attached directly to the interior surface (or to a lens or light control film or coating positioned between the interior surface and one or more of the emitters 744, 746, 752, 754 or photodetectors 748, 756), or one or more modules including the groups 742, 750 of sensing components may be attached directly to the interior surface (or to a lens or light control film or coating positioned between the interior surface and one or more of the emitters 744, 746, 752, 754 or photodetectors 748, 756). Alternatively, the groups 742, 750 of sensing components may be attached to a substrate or module that is attached directly to the interior surface of the second back cover portion 214-2 (or to a lens or light control film or coating positioned between the interior surface and the substrate or module). The second back cover portion 214-2 may similarly be attached to the first back cover portion 214-1 using an adhesive. The adhesives may be the same or different.

The off-axis positioning of the groups 742, 750 of sensing components may enable the sensing components to avoid a liquid 802 (e.g., water or perspiration) that happens to be on the object 804, which liquid may tend to be attracted toward an apex (e.g., the center axis 324) of the second back cover portion 214-2. The off-axis positioning of the groups 742, 750 of sensing components may also enable a device to collect multiple sets of measurements (e.g., a set of measurements from each group 742, 750). In some cases, a tilt of the second back cover portion 214-2 with respect to the object 804 may make one of the other sets of measurements more useful, or the sets of measurements may be averaged or otherwise combined or used when both sets of measurements are considered useful. Still further, measurements generated by the different groups 742, 750 of sensing components may in some cases be used as stereo measurements, and may be used to determine a distance to an object.

The groups 742, 750 of sensing components may be directly or indirectly connected to circuitry 808 (e.g., a processor (e.g., a general purpose processor programmed by suitable machine-readable instructions or software) and/or other circuitry, which in some cases may include the processor described with reference to FIG. 1 or 2A-2B) that includes, or is configured to operate as, a timing circuit, a matter differentiation circuit, and a proximity detection circuit. The proximity detection circuit may be configured to indicate a proximity of a device (e.g., the second back cover portion 214-2) to an object 804. The proximity indication may be based at least in part on a first amount of electromagnetic radiation received by the photodetector 748 after the emitter 744 emits a first beam of electromagnetic radiation, and a second amount of electromagnetic radiation received by the photodetector 748 after the emitter 746 emits a second beam of electromagnetic radiation. In some cases the proximity indication may be a discrete value. In other cases, the proximity indication may identify one of at least two different ranges of proximities.

The proximity indication may also be based on a third amount of electromagnetic radiation received by the photodetector 756 after the emitter 752 emits a third beam of electromagnetic radiation, and a fourth amount of electromagnetic radiation received by the photodetector 756 after the emitter 754 emits a fourth beam of electromagnetic radiation. For example, ratios of amounts of electromagnetic radiation of a first IR wavelength to amounts of electromagnetic radiation of a second IR wavelength may be computed for each group 742, 750 of sensing components, and a comparison of the ratios may indicate an amount of tilt of the second back cover portion 214-2 with respect to the object 804.

Figure 9A:
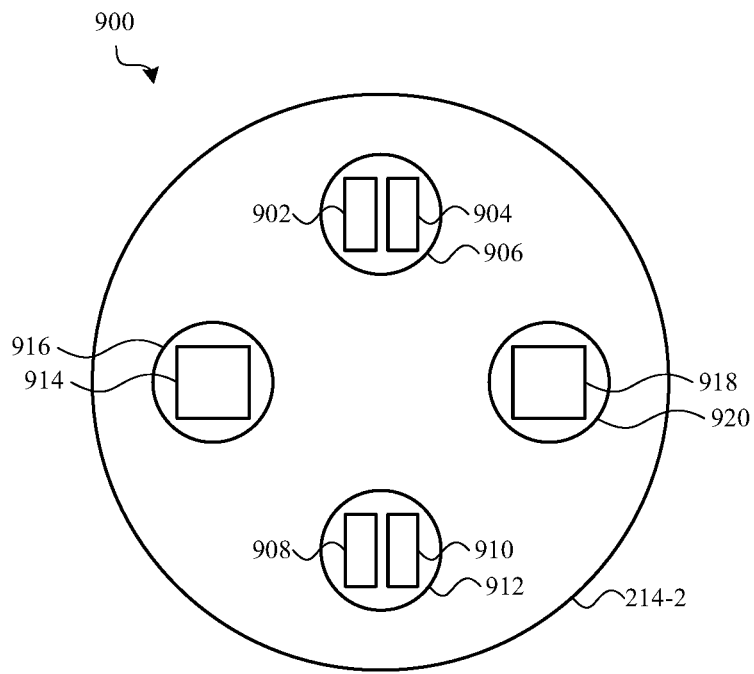
FIGS. 9A and 9B show example plan views of skin-facing sensors (or sensor systems) that may be included in the device described with reference to FIG. 1, 2A-2B, or 4A-4B.

FIG. 9A shows an example plan view of a skin-facing sensor (or sensor system 900) that may be included in the device described with reference to FIG. 1, 2A-2B, or 4A-4B. By way of example, the sensor system 900 is shown to be positioned under a back or back cover of a housing (e.g., under the second back cover portion 214-2 described with reference to FIG. 2B).

The sensor system 900 is shown to include a first pair of electromagnetic radiation emitters 902, 904 that emit electromagnetic radiation through a first window 906 in the second back cover portion 214-2, and a second pair of electromagnetic radiation emitters 908, 910 that emit electromagnetic radiation through a second window 912 in the second back cover portion 214-2. In some embodiments, the first emitter 902 may emit electromagnetic radiation at 1300 nm or 1650 nm; the second emitter 904 may emit electromagnetic radiation at 1200 nm; the third emitter 908 may emit electromagnetic radiation at 1050 nm; and the fourth emitter 910 may emit electromagnetic radiation at 1450 nm. In alternative arrangements, the emitters may emit other wavelengths of electromagnetic radiation, or some of the emitters may emit the same wavelength of electromagnetic radiation.

The sensor system 900 may also include a first photodetector 914 that receives reflected or backscattered electromagnetic radiation through a third window 916, and a second photodetector 918 that receives reflected or backscattered electromagnetic radiation through a fourth window 920.

In operation, the emitters 902, 904, 908, 910 may be sequentially activated, and an amount of reflected or backscattered electromagnetic radiation of each emitted wavelength may be detected by each photodetector 914, 918. The different distances between each emitter and each photodetector 914, 918 may assist in determining the accuracy (or validity) of the amounts of reflected or backscattered electromagnetic radiation received by the photodetectors 914, 918, and in some cases may improve matter differentiation decisions made by a matter differentiation circuit.

Figure 9B:
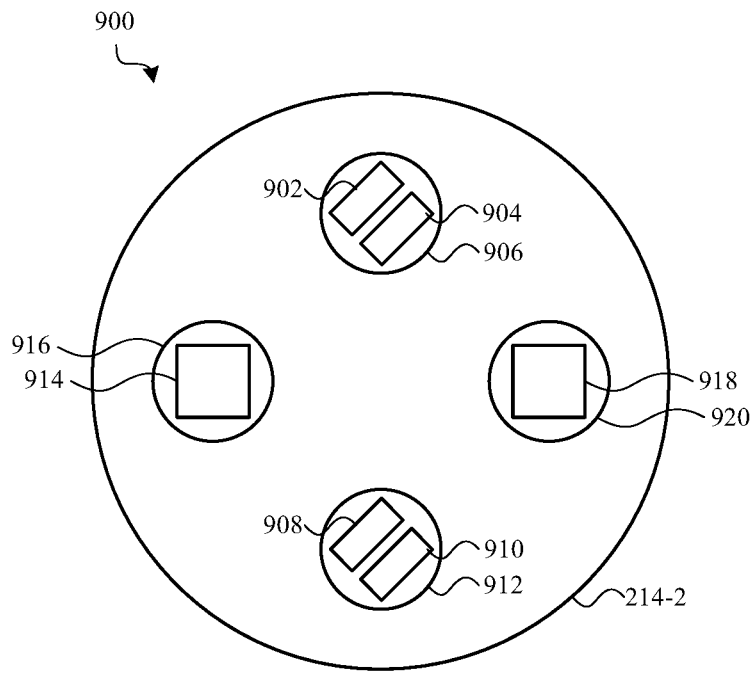

FIG. 9B shows an alternative arrangement of the components described with reference to FIG. 9A, in which each of the emitters 902, 904, 908, 910 has been rotated by 45 degrees. Such a rotation may place the emitters of a pair of emitters at a same distance from one of the photodetectors 914 or 918, and at different distances to the other of the photodetectors 914 or 918.

FIG. 10A shows an example plan view of a Fresnel lens 1000 positioned over a group of sensing components including the emitters 302, 304 and photodetector 306 described with reference to FIGS. 3A-3B. The Fresnel lens 1000 may include one or multiple Fresnel cells. Alternatively, a different type of lens, or a stack of lenses, may be positioned over the group of sensing components. The Fresnel lens 1000 (or other type(s) of lens(es)) may be positioned between a device housing and the group of sensing components (e.g., between the second back cover portion 214-2 and the emitters 302, 304 and photodetector 306).

A set of one or more IR wavelength-blocking walls 1002 may be optionally disposed between the photodetector 306 and the emitters 302, 304, as described, for example, with reference to FIG. 3A. The wall(s) may extend from a substrate, to which the photodetector 306 and emitters 302, 304 are attached, to an interior surface of the lens 1000, or may alternatively extend through the lens 1000 and/or second back cover portion 214-2.

FIG. 10B shows an example plan view of a set of Fresnel lenses 1010, 1012, 1014, with each of the Fresnel lenses 1010, 1012, 1014 positioned over a respective sensing component of a group of sensing components. For example, a first Fresnel lens 1010 is positioned over the first emitter 302 described with reference to FIGS. 3A-3B; a second Fresnel lens 1012 is positioned over the second emitter 304; and a third Fresnel lens 1014 is positioned over the photodetector 306. Alternatively, one or more of the Fresnel lenses 1010, 1012, 1014 may be replaced by a different type of lens or a stack of lenses. The Fresnel lenses 1010, 1012, 1014 (or other type(s) of lens(es)) may be positioned between a device housing and each of the sensing components (e.g., between the second back cover portion 214-2 and the first emitter 302, second emitter 304, or photodetector 306).

In other lens arrangements, a lens or lens stack may be disposed between a housing and any subset of sensing components, or no type of lens or lens stack may be disposed between the housing and one or more of the sensing components.

FIG. 11A shows an example plan view of an LCF 1100 positioned over a group of sensing components including the emitters 302, 304 and photodetector 306 described with reference to FIGS. 3A-3B. The LCF 1100 may be positioned between a device housing and the group of sensing components (e.g., between the second back cover portion 214-2 and the emitters 302, 304 and photodetector 306). Alternatively, different segments or types of LCF may be positioned over different sensing components, or no LCF may be positioned over one or more sensing components, or different segments or types of LCF positioned over different sensing components may be oriented to guide or block electromagnetic radiation that is emitted, reflected, or backscattered at different incident angles with respect to a surface of the LCF 1100. In some embodiments, the LCF 1100 may be replaced or supplemented with an LVF, BP filter, or polarizer.

A set of one or more IR wavelength-blocking walls 1102 may be optionally disposed between the photodetector 306 and the emitters 302, 304, as described, for example, with reference to FIG. 3A. The wall(s) may extend from a substrate, to which the photodetector 306 and emitters 302, 304 are attached, to an interior surface of the LCF 1100, or may alternatively extend through the LCF 1100 and/or second back cover portion 214-2.

FIG. 11B shows an example plan view of different LCFs 1110, 1112 positioned over different sets of the sensing components described with reference to FIGS. 3A-3B. For example, a first LCF 1110 may be positioned over the photodetector 306, and a second LCF 1112 may be positioned over the emitters 302, 304. The first LCF 1110 may have the same or different properties as the second LCF 1112. For example, and in some embodiments, the louvers of the first LCF 1110 may be rotated 90 degrees with respect to the louvers of the second LCF 1112.

In some embodiments, the LCFs described with reference to FIG. 11A or 11B may alternatively be polarizers. In some cases, a set of one or more LCFs or polarizers may be used to increase the received signal strength for reflected or backscattered electromagnetic radiation resulting from volume scattering and/or decrease the received signal strength for reflected or backscattered electromagnetic radiation resulting from surface scattering. For example, the LCF 1112 may have louvers that tilt emitted electromagnetic radiation away from the photodetector 306, and/or the LCF 1110 may have louvers that limit the photodetector's receipt of electromagnetic radiation to incident angles that are oriented away from the emitters 302, 304. Alternatively, the LCFs 1110, 1112 may be replaced with polarizers having different polarization directions. As another alternative, light pipes or electromagnetic radiation waveguides may be used to control the directions in which the emitters 302, 304 emit and the photodetector 306 receives. The use of LCFs and/or polarizers can be especially useful for reducing optical crosstalk between emitters and a photodetector, and for weighting the effects of volume scattering of photons more heavily than the effects of surface scattering of photons.

FIGS. 12A-12D show various example elevations of first and second beams 1200, 1202 of electromagnetic radiation having different IR wavelengths, as emitted by first and second emitters 1204, 1206. Reflections or backscatters of the beams 1200, 1202 may be received by a photodetector 1208. In some embodiments, the first and second emitters 1204, 1206 may be the first and second emitters described with reference to FIGS. 3A-3B, and the photodetector 1208 may be the photodetector described with reference to FIGS. 3A-3B.

The emitters 1204, 1206 may be separated from the photodetector 1208 by a set of one or more IR wavelength-blocking walls disposed between the photodetector 1208 and each of the first and second emitters 1204, 1206. In some cases, the set of one or more IR wavelength-blocking walls may include the single light-blocking wall 1210 shown in FIGS. 12A-12D. In other cases, an IR wavelength-blocking wall may be formed around the photodetector 1208, or around one or both or each of the emitters 1204, 1206, or around each of the photodetector 1208, the first emitter 1204, and the second emitter 1206. Each IR-wavelength blocking wall 1210 may extend between a substrate (or substrates) to which the emitters 1204, 1206 and photodetector 1208 are attached to an interior surface 1212 of a back or back cover 1214 of a housing (e.g., an interior surface of the second back cover portion described with reference to FIGS. 2A-2B and 3A-3B). Alternatively, one or more of the IR wavelength-blocking walls 1210 may extend through the back or back cover 1214 of the housing (e.g., to the exterior surface 1216 of the back or back cover 1214). In other examples, there may be no IR wavelength-blocking walls 1210.

Figure 12A:
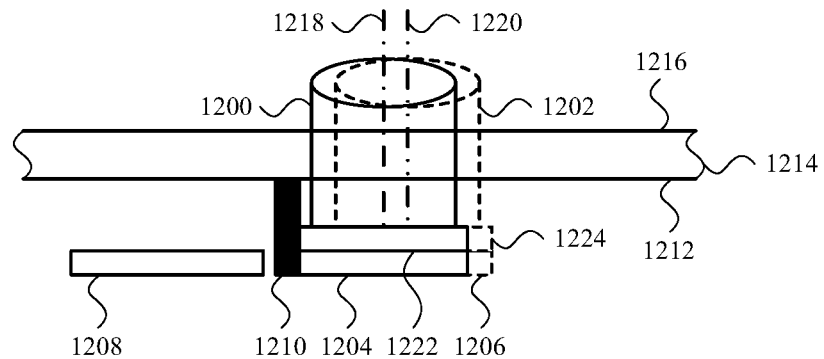
FIGS. 12A-12D show various example elevations of first and second beams of electromagnetic radiation having different IR wavelengths, as emitted by the first and second emitters.

As shown in FIG. 12A, the first and second emitters 1204, 1206 may in some cases emit beams 1200, 1202 of electromagnetic radiation along axes 1218, 1220 that are perpendicular to electromagnetic radiation emission surfaces of the emitters 1204, 1206. In some cases, the beams 1200, 1202 may fan out as they propagate along the axes 1218, 1220. In other cases, the beams 1200, 1202 may be collimated or converge. In some embodiments, an electromagnetic radiation beam director 1222 or 1224 (e.g., a lens, lenses, LCF(s), polarizer(s), light guide(s), electromagnetic radiation waveguide(s), or other passive or active component) may be positioned in the path of one or both of the beams 1200, 1202, and may collimate or otherwise alter the direction or shape of the beam 1200 and/or 1202. In some embodiments, one electromagnetic radiation beam director (or a common set) may alter the direction or shape of both beams 1200, 1202.

Figure 12B:
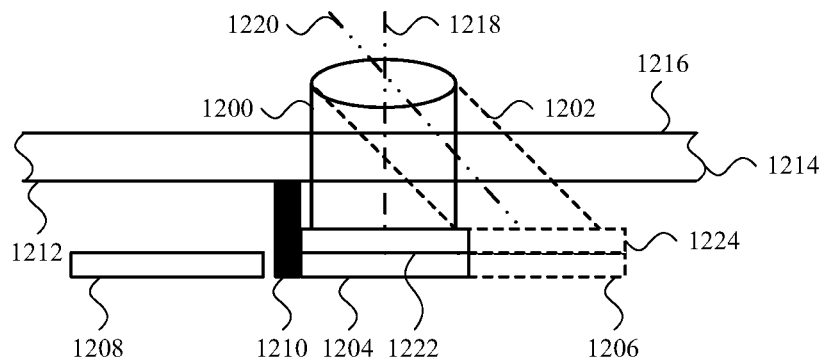

As shown in FIG. 12B, one of the first or second emitter 1204 or 1206 may emit a beam 1200 of electromagnetic radiation along an axis 1218 that is perpendicular to an electromagnetic radiation emission surface of the emitter, and the other emitter 1204 or 1206 may emit a beam 1202 of electromagnetic radiation along an axis 1220 that is tilted with respect to an electromagnetic radiation emission surface of the emitter. In some cases, the beams 1200, 1202 may fan out as they propagate along the axes 1218, 1220. In other cases, the beams 1200, 1202 may be collimated or converge. In some embodiments, an electromagnetic radiation beam director may be positioned in the path of one or both of the beams 1200, 1202, and may collimate or otherwise alter the direction or shape of the beam 1200 and/or 1202. In some embodiments, one electromagnetic radiation beam director (or a common set) may alter the direction or shape of both beams 1200, 1202.

Figure 12C:
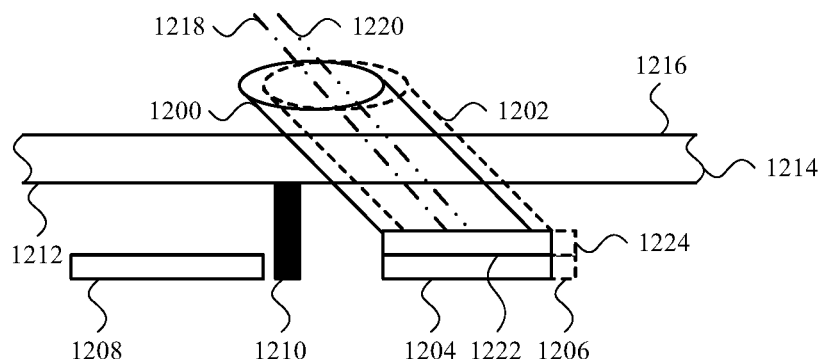
Figure 12D:
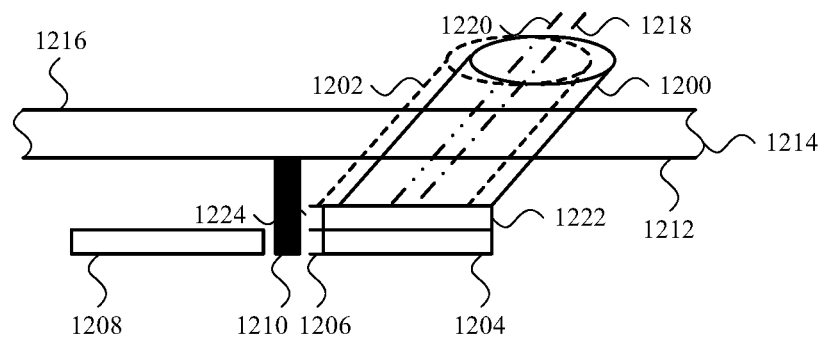

By way of example, the second beam 1202 is shown to have an axis 1220 that is tilted toward the photodetector 1208. Alternatively, the second beam 1202 may have an axis 1220 that is tilted away from the photodetector 1208. Titling the axis 1220 of the second beam 1202 may tend to decrease or increase (or just change) the propagation path of emitted electromagnetic radiation, which may tend to decrease or increase the likelihood or percentage of electromagnetic radiation that may be reflected or backscattered toward the photodetector 1208. This may change the ratio of amounts of different wavelengths of electromagnetic radiation received/detected by the photodetector 1208, which may improve a device's ability to differentiate different types of matter against which the back cover 1214 is placed. In some embodiments, the axes 1218, 1220 of both beams 1200, 1202 may be tilted toward the photodetector 1208 (as shown in FIG. 12C), or away from the photodetector 1208 (as shown in FIG. 12D).

Figure 13A:
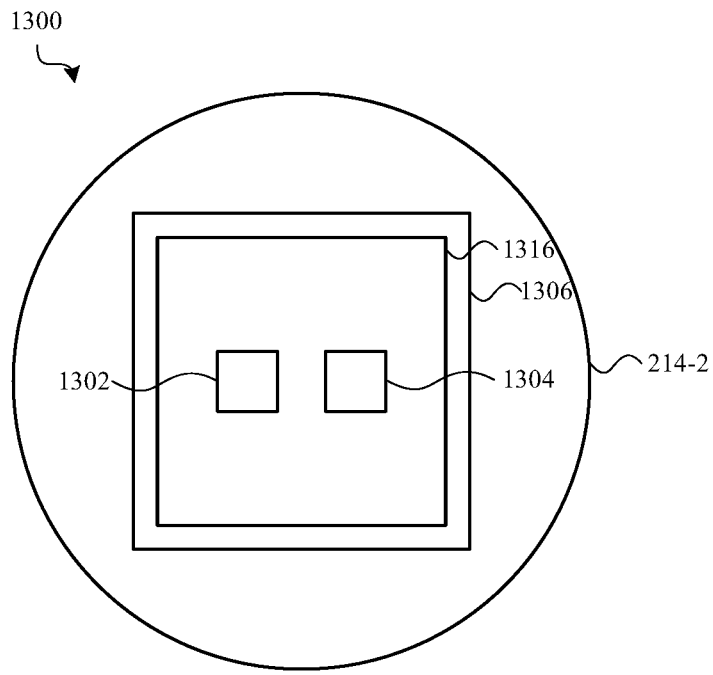
FIGS. 13A and 13B show another example of a skin-facing sensor (or sensor system) that may be included in the device described with reference to FIG. 1, 2A-2B, 3A-3B, or 4A-4B.
Figure 13B:
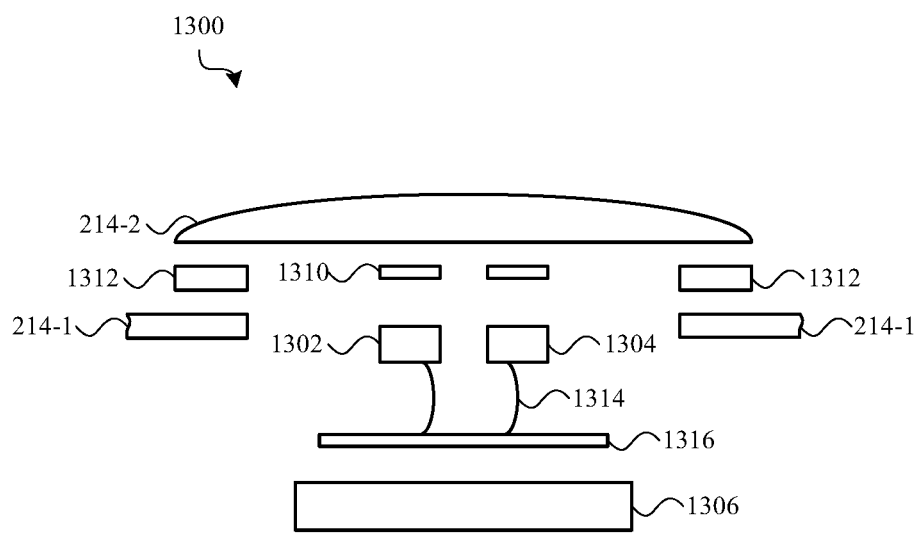

FIGS. 13A and 13B show an example of a skin-facing sensor (or sensor system 1300) that may be included in the device described with reference to FIG. 1, 2A-2B, 3A-3B, or 4A-4B. By way of example, the sensor system 1300 is shown to be positioned under a back or back cover of a housing (e.g., under the second back cover portion 214-2 described with reference to FIG. 2B). FIG. 13A shows a plan view of the sensor system 1300, and FIG. 13B shows an elevation of the sensor system 1300.

By way of example, and as shown in FIG. 13A, the sensor system 1300 may include first and second proximity sensors 1302, 1304. By way of example, the first proximity sensor 1302 may be a pressure sensor, a capacitive sensor, an optical sensor, or another type of proximity sensor. Also by way of example, the second proximity sensor 1304 may be a capacitive sensor, an optical sensor, or another type of proximity sensor. The first proximity sensor 1302 may be configured to detect an object within a first range of proximities to the back or back cover of the housing, such as a range of proximities that is closer to the second back cover portion 214-2. The second proximity sensor 1304 may be configured to detect an object within a second range of proximities to the back or back cover of the housing, such as a range of proximities that extends farther from the second back cover portion 214-2 than the first range of proximities. The first and second ranges of proximities may be overlapping or non-overlapping (e.g., adjacent).

In some embodiments, the first and second proximity sensors 1302, 1304 may be connected to circuitry 1306 (e.g., a processor (e.g., a general purpose processor programmed by suitable machine-readable instructions or software) and/or other circuitry, which in some cases may include the processor described with reference to FIG. 1 or 2A-2B) that includes, or is configured to operate as, a proximity sensor management circuit. The proximity sensor management circuit may be configured to activate the first proximity sensor 1302 repeatedly or continually over a period of time, to generate a series of measurements indicating whether an object (e.g., a wrist of a user) is within the first range of proximities. By default, the proximity sensor management circuit may maintain the second proximity sensor 1304 in an inactive state. The proximity sensor management circuit may selectively activate the second proximity sensor 1304, during the period of time in which the first proximity sensor 1302 is active, when the series of measurements generated by the first proximity sensor 1302 satisfy a set of one or more conditions. Similarly, the proximity sensor management circuit may selectively deactivate the second proximity sensor 1304, during the period of time in which the first proximity sensor 1302 is active, when the series of measurements generated by the first proximity sensor 1302 satisfy a second set of one or more conditions. Selective activation/deactivation of the second proximity sensor 1304 may be useful, for example, when the second proximity sensor 1304 consumes more power when activated (or in use) than the first proximity sensor 1302 consumes when activated (or in use). In some cases, the second proximity sensor 1304 may consume more power, at least in part, because it has a higher sample rate (e.g., acquires more measurements) than the first proximity sensor 1302. In some cases, the first proximity sensor 1302 may be a lower cost and/or less accurate proximity sensor than the second proximity sensor 1304.

In some embodiments, the set of one or more conditions that need to be satisfied for the second proximity sensor 1304 to be activated may include a measurement, in the series of measurements, that indicates an object (e.g., a wrist) is outside the first range of proximities. In some embodiments, the set of one or more conditions may include a number of measurements, in the series of measurements generated by the first proximity sensor 1302, that indicate the object is outside the first range of proximities. The number of measurements may exceed a threshold number greater than one. In some embodiments, the set of one or more conditions may include a change in value in the series of measurements, which change in value exceeds a threshold change. In some embodiments, the set of one or more conditions may include a rate of change in value in the series of measurements, which rate of change in value exceeds a threshold rate of change. A change in value that exceeds a threshold, or a rate of change in value that exceeds a threshold, may indicate, for example, that the object is moving toward or out of the usable range of the first proximity sensor 1302. Similarly to the set of one or more conditions that need to be satisfied to activate the second proximity sensor 1304, the second set of one or more conditions, that need to be satisfied for the second proximity sensor 1304 to be deactivated, may include a particular measurement, number of measurements, change in value of measurements, or rate of change in value of measurements.

In some embodiments, the proximity sensor management circuit may be configured to activate both the first and second proximity sensors 1302, 1304 repeatedly or continually over a period of time, to generate first and second respective series of measurements indicating whether an object (e.g., a wrist of a user) is within the first range of proximities. In some cases the first range of proximities may be a range that requires contact and/or near contact between a device (e.g., the second back cover portion 214-2) and the object (e.g., a user's wrist). In these cases, a comparison of the measurements obtained from the first and second proximity sensors 1302, 1304 (e.g., a ratio or difference of the measurements), or a comparison of the proximities indicated by the measurements (e.g., a ratio or difference of indicated proximities) may provide an additional check to confirm whether the device is, in fact, within the first proximity range (e.g., that the device and object are in contact). For example, the measurements obtained from the different proximity sensors 1302, 1304 may approach a common asymptote within the first proximity range (e.g., when the object is in contact with the device), such that a ratio of the measurements is very high (e.g., near 1.0) when both measurements indicate that the object is within the first proximity range. However, the measurements may be fairly different, and their ratio may be significantly less than 1.0, when the measurements indicate that the object is outside the first proximity range. In some cases, both proximity sensors 1302, 1304 may be activated in parallel, within the first proximity range (or regardless of whether an object is within the first proximity range) when a processor or application needs to know whether an object is in contact with a device for purposes of acquiring valid sensor measurements. Power savings may be achieved in these contexts by deactivating the sensor that requires contact between the device and the object until the first and second proximity sensors 1302, 1304 indicate individually and in combination that the object is in contact with the device.

As shown in the exploded view of FIG. 13B, the first and second proximity sensors 1302, 1304 may be attached to an interior surface of the second back cover portion 214-2 using an adhesive 1310. The proximity sensors 1302, 1304 may be attached to the interior surface of the second back cover portion 214-2 apart from other components of a device housing. In some embodiments, the proximity sensors 1302, 1304, or components thereof, may be attached directly to the interior surface, or one or more modules including the proximity sensors 1302, 1304 may be attached directly to the interior surface. Alternatively, the proximity sensors 1302, 1304 may be attached to a substrate or module that is attached directly to the interior surface of the second back cover portion 214-2. The second back cover portion 214-2 may similarly be attached to the first back cover portion 214-1 using an adhesive 1312. The adhesives 1310, 1312 may be the same or different. The adhesive 1312 may in some cases be a ring of adhesive disposed around the perimeter of the second back cover portion 214-2. The first and second proximity sensors 1302, 1304 may be electrically connected to the circuitry 1306 (e.g., to an integrated circuit (IC) or printed circuit board (PCB)). In some cases, the first and second emitters 302, 304 and/or photodetector 306 may be electrically connected to the circuitry 1306 via a set of fly wires 1314 and/or a flex circuit 1316.

In some embodiments, a visibly opaque ink may be applied to the interior surface of the second back cover portion 214-2, in at least a region or regions disposed between the first and second proximity sensors 1302, 1304, on one side, and the second back cover portion 214-2 on the other side.

Figure 14A:
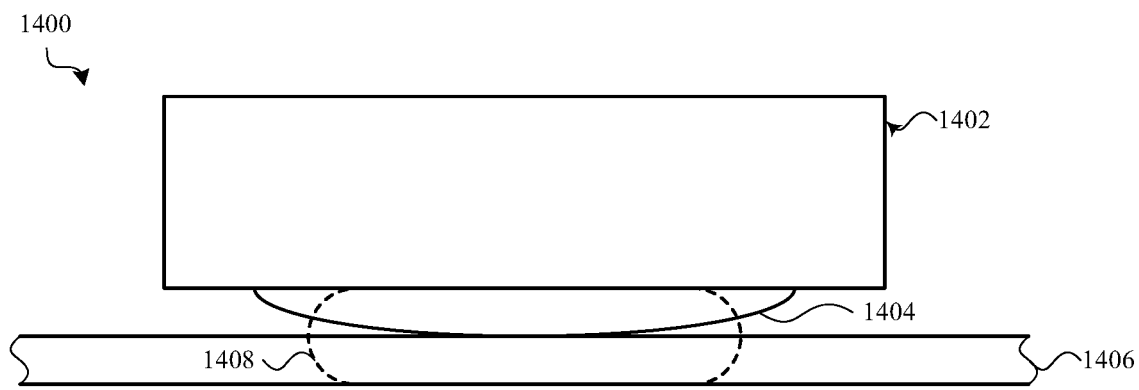
FIGS. 14A-14C show an example of a device having a housing, in which a back or back cover of the housing is positioned against or at varying distances from an object.
Figure 14B:
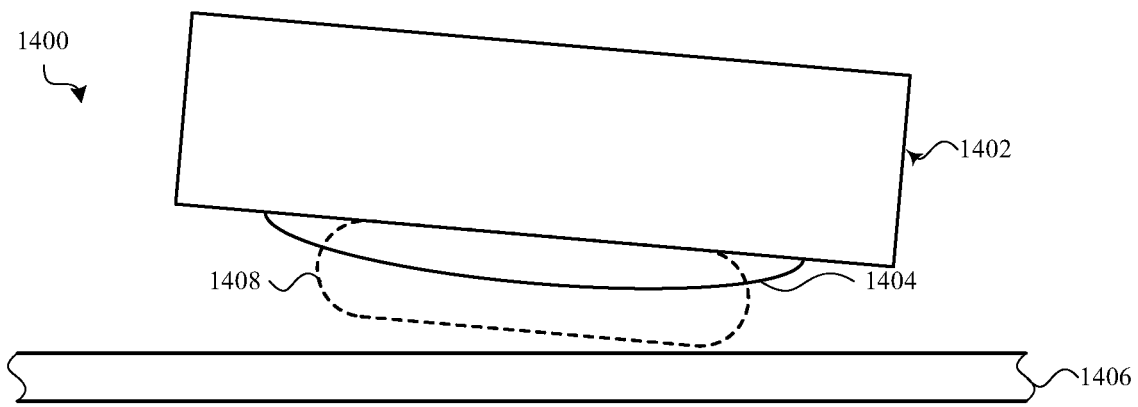
Figure 14C:
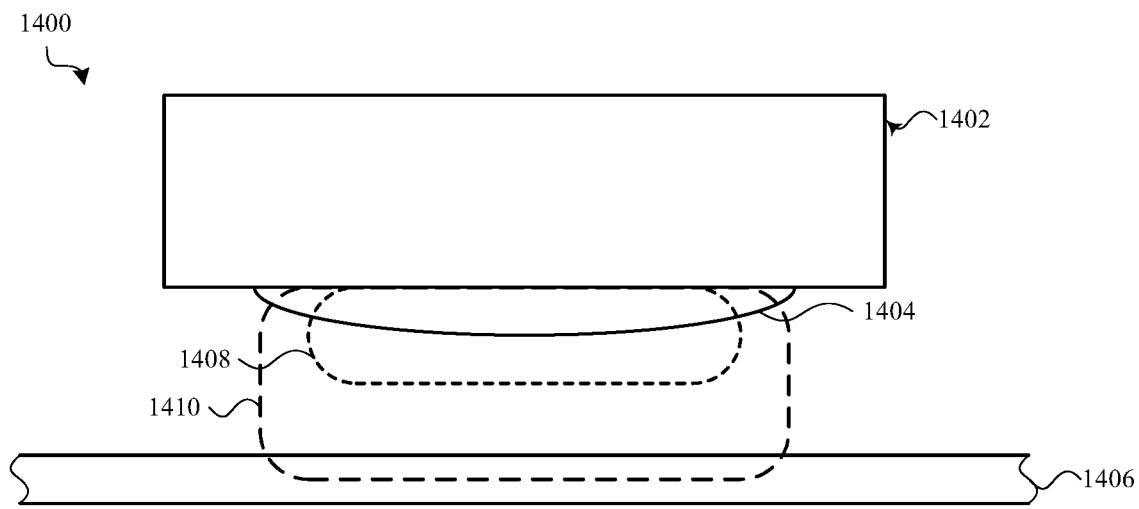

FIGS. 14A-14C show an example of a device 1400 (e.g., an electronic watch or smart watch) having a housing 1402, in which a back 1404 or back cover of the housing 1402 is positioned against or at varying distances from an object 1406 (e.g., a user's wrist). The device 1400 may be an example of the devices described with reference to FIG. 1, 2A-2B, or 4A-4B. FIG. 14A shows the back 1404 of the housing 1402 positioned against or close to the object 1406; FIG. 14B shows the back 1404 of the housing 1402 positioned farther away from the object 1406 than what is shown in FIG. 14A; and FIG. 14C shows the back 1404 of the housing 1402 positioned farther away from the object 1406 than what is shown in FIG. 14B.

When the device 1400 is a wearable device, the position of the device 1400 in FIG. 14A may be consistent with the device 1400 being worn and positioned against a user's skin (e.g., a wrist). A wearable device, when worn, will typically spend most of its time in the position shown in FIG. 14A. The position of the device 1400 in FIG. 14B may be consistent with the device 1400 being somewhat loosely worn, such that it may occasionally tilt with respect to, or separate from, the user's skin. The position of the device 1400 in FIG. 14B may also be consistent with the device 1400 being temporarily dislodged from the user's skin due to a shock or the user repositioning the device 1400. The position of the device 1400 in FIG. 14C may be consistent with the device 1400 being removed, or consistent with the device 1400 being more loosely worn than in FIG. 14A or 14B, such that the proximity of the device 1400 to the user's skin may only be detected using, for example, the second proximity sensor described with reference to FIG. 13.

For the description contained in the next few paragraphs, it will be assumed that the device 1400 includes the sensor system described with reference to FIG. 13 and, particularly, the first and second proximity sensors 1302, 1304 and circuitry 1306 configured to operate as a proximity sensor management circuit.

In some embodiments, the proximity sensor management circuit may be configured to determine whether the object 1406 (e.g., skin, or a user's wrist) is within a first range of proximities 1408, using the first proximity sensor 1302, while maintaining the second proximity sensor 1304 in an inactive state. The object 1406 is within the first range of proximities 1408 in FIG. 14A. In some cases, the proximity sensor management circuit may determine, using the first proximity sensor 1302, that the object 1406 has moved outside the first range of proximities 1408, as shown in FIG. 14B or 14C. If the object 1406 moves outside the first range of proximities 1408 for less then a predetermined period of time (e.g., less than a short period of time), or for fewer than a threshold number of times within a predetermined evaluation period, the proximity sensor management circuit may continue to maintain the second proximity sensor in the inactive state. This state of operation is represented, for example, by one or more movements of the device 1400 between the state shown in FIG. 14A and the state shown in FIG. 14B. After the device 1400 moves outside the first range of proximities 1408, or after the device 1400 moves outside the first range of proximities 1408 for more than the predetermined period of time and/or more than the threshold number of times, the proximity sensor management circuit may transition the second proximity sensor 1304 from the inactive state to an active state and scan for the object within a second range of proximities 1410 using the second proximity sensor 1304. In some embodiments, the proximity sensor management circuit may also scan for the object 1406 within the first range of proximities 1408, using the first proximity sensor 1302, while the second proximity sensor 1304 is used to scan for the object within the second range of proximities 1410. In some embodiments, the proximity sensor management circuit may transition the first proximity sensor 1302 to an inactive state after the second proximity sensor 1304 is activated.

The proximity sensor management circuit may be further configured to determine, while the second proximity sensor 1304 is active, that the object 1406 is outside the second range of proximities 1410. After determining the object 1406 is outside the second range of proximities 1410, the proximity sensor management circuit may transition the second proximity sensor 1304 from the active state to the inactive state. The proximity sensor management circuit may also or alternatively be configured to determine, while the second proximity sensor 1304 is active, that the object is within the first range of proximities 1408. After determining the object 1406 is within the first range of proximities 1408, the proximity sensor management circuit may transition the second proximity sensor 1304 from the active state to the inactive state.

In some cases, the first and second ranges of proximities 1408, 1410 may both be consistent with the device 1400 being worn. In these cases, the circuitry 1306 (e.g., a processor) may be configured to distinguish between proximity ranges of the back 1404 of the housing 1402 to the object 1406 using outputs of the first proximity sensor 1302 and the second proximity sensor 1304. For example, when the output of the first proximity sensor 1302 indicates a detection of the object 1406 within the first range of proximities 1408, the processor may be configured to generate a first indication that the back 1404 of the housing 1402 is in close proximity to the object 1406; and when the output of the second proximity sensor 1304 indicates a detection of the object 1406 within the second range of proximities 1410 while the output of the first proximity sensor 1302 indicates no detection of the object 1406 within the first range of proximities 1408, the processor may be configured to generate a second indication that the back 1404 of the housing 1402 is farther from the object 1406 than the close proximity.

In some cases, the first range of proximities 1408 may be consistent with the device 1400 likely being on a user (e.g., worn by the user, or on-wrist), and the second range of proximities 1410 may be consistent with the device 1400 being off a user (e.g., not worn by the user, or off-wrist). In these cases, the circuitry 1306 (e.g., a processor) may be configured to distinguish between whether the wearable device is likely on or off of a user (e.g., between a likely on state and a likely off state) using outputs of the first proximity sensor 1302 and the second proximity sensor 1304. For example, when the output of the first proximity sensor 1302 indicates a detection of the object 1406 within the first range of proximities 1408, the processor may be configured to indicate an existence of the likely on state; and when the output of the second proximity sensor 1304 indicates a detection of the object 1406 within the second range of proximities 1410 while the output of the first proximity sensor 1302 indicates no detection of the object 1406 within the first range of proximities 1408, the processor may be configured to indicate an existence of the likely off state.

Figure 15A:
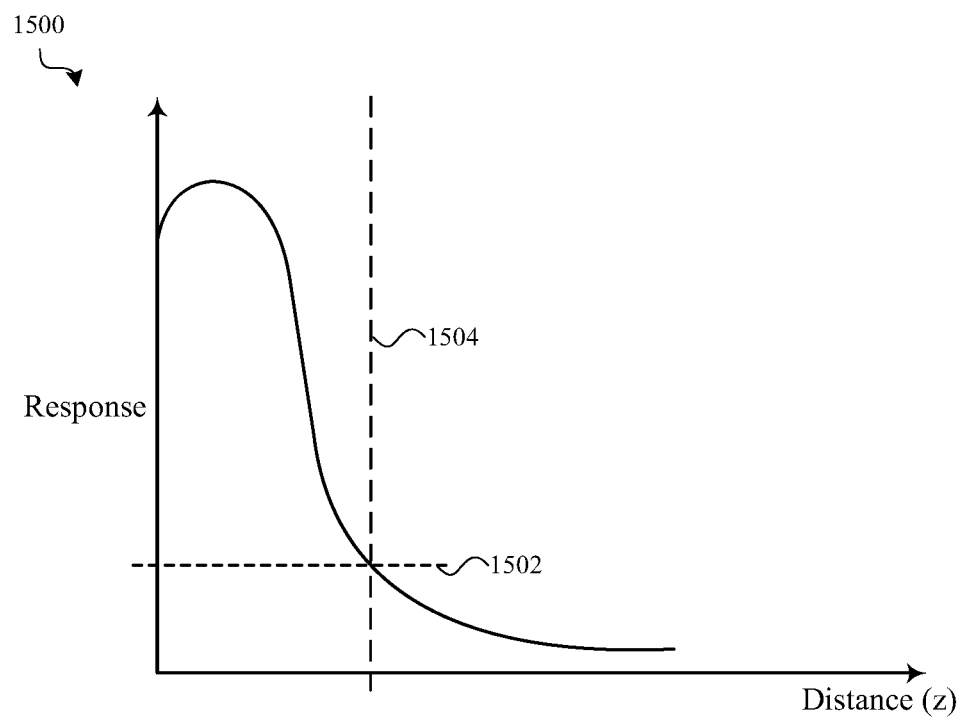
FIGS. 15A and 15B show example conditions that may be used to trigger the activation of the second proximity sensor described with reference to FIGS. 13A-14B.
Figure 15B:
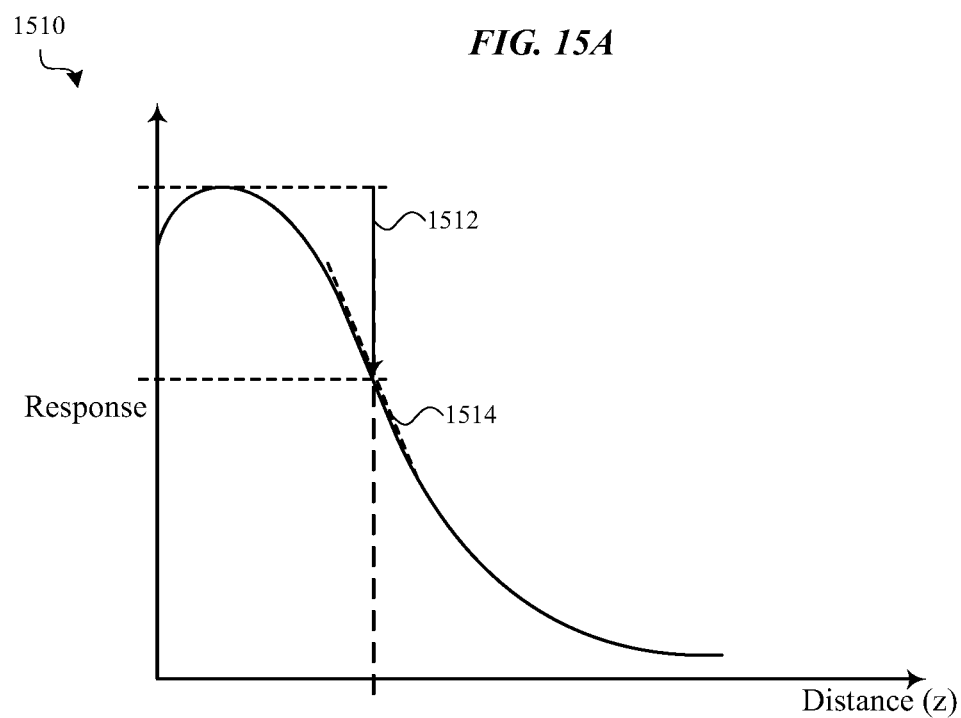

FIGS. 15A and 15B show example conditions that may be used to trigger the activation of the second proximity sensor 1304 described with reference to FIGS. 13A-14B. As shown in FIG. 15A, the first proximity sensor 1302 described with reference to FIGS. 13A-14B may have a response 1500 (e.g., an output) that varies with a proximity of an object to the sensor (e.g., a distance z between the object and the sensor). Typically, the sensor's response 1500 will have a maximum value (or peak value) at some distance z, and trail off on either side of the maximum value. Often, but not always, the trailing off of the sensor's response 1500 will be most significant at greater distances (e.g., greater values of z). Above some distance of z, the response 1500 of the first proximity sensor 1302 may become unreliable. For example, above some value of z, the response 1500 of the first proximity sensor 1302 may be less accurate or be indistinguishable from noise. The response 1500 may have a value 1502 (i.e., a threshold), below which the response 1500 is considered unreliable. The value 1502, or a value of the response 1500 that is somewhat higher than the value 1502, may define a boundary 1504 between first and second proximity ranges. When the output of the first proximity sensor 1302 drops below the value 1502, or drops below the value 1502 for a threshold number of times, the proximity sensor management circuit described with reference to FIGS. 13A-14B may transition the second proximity sensor 1304 from its inactive state to its active state.

FIG. 15B shows another example response 1510 (or output) of the first proximity sensor 1302 described with reference to FIGS. 13A-14B. Similarly to the response described with reference to FIG. 15A, the response 1510 may vary with a proximity of an object to the sensor (e.g., a distance z between the object and the sensor). Typically, the sensor's response 1510 will have a maximum value (or peak value) at some distance z, and trail off on either side of the maximum value. Often, but not always, the trailing off of the sensor's response 1510 will be most significant at greater distances (e.g., greater values of z).

As discussed with reference to FIGS. 13A-13B, and in some embodiments, the set of one or more conditions that need to be satisfied for the second proximity sensor 1304 to be activated may include a change in value in a series of measurements, which change in value exceeds a threshold change. In some embodiments, the set of one or more conditions may include a rate of change in value in the series of measurements, which rate of change in value exceeds a threshold rate of change. Examples of such changes are represented in FIG. 15B by a threshold change 1512 in response values (i.e., measurements) and a threshold rate of change 1514 in response values. The threshold change 1512 may occur at various points along the response curve, but is unlikely to occur within a window of proximities about the maximum value of the response 1510 (e.g., because the response 1510 does not change this much near the maximum value). The threshold rate of change 1514 (or threshold slope of the response 1510) can likewise be selected so that the threshold rate of change 1514 is unlikely to be met within a window of proximities about the maximum value of the response 1510.

In some cases, the conditions described with reference to FIG. 15A may be more suitable for activating the second proximity sensor 1304 when the first proximity sensor 1302 is a response with sharper roll off about the response's maximum value; and the conditions described with reference to FIG. 15B may be more suitable for activating the second proximity sensor 1304 when the first proximity sensor 1302 has a response with slower roll off about the response's maximum value.

In some embodiments, the conditions described with reference to FIG. 15A or 15B may be subjected to hysteresis (e.g., a time-varying average), to prevent activation of the second proximity sensor 1304 under conditions such as those described with reference to FIGS. 14A and 14B, where a device is temporarily struck, moved, or jostled, leading to intermittent or short-term measurements suggesting a back or back cover of a housing has moved farther away from an object (e.g., a user's wrist).

Figure 16A:
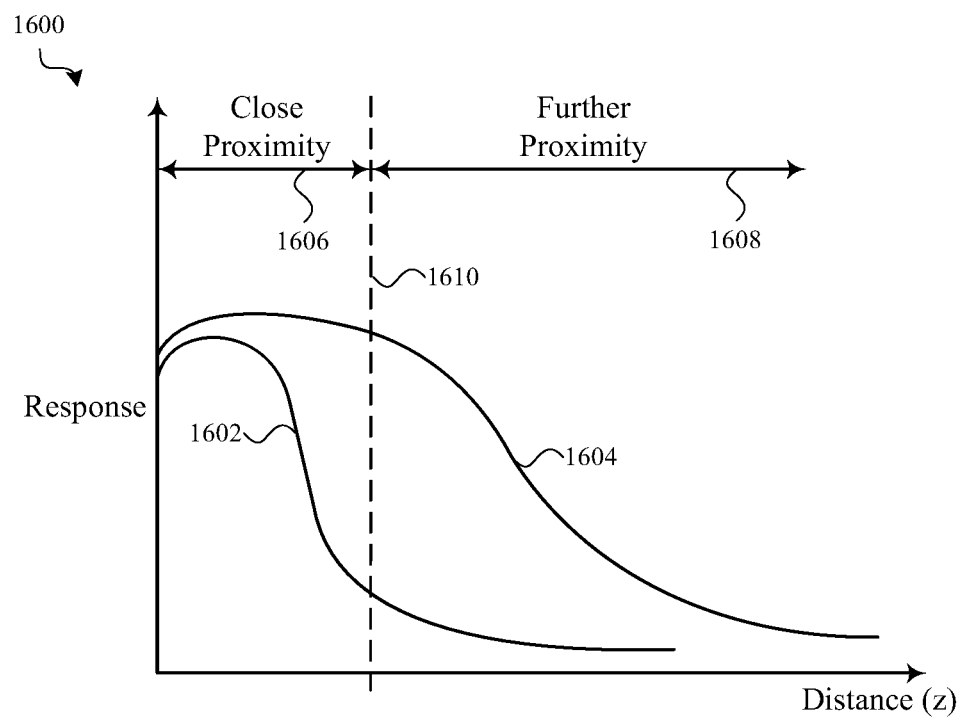
FIGS. 16A and 16B show example relationships between the measurements of the proximity sensors described with reference to FIGS. 13A-13B.
Figure 16B:
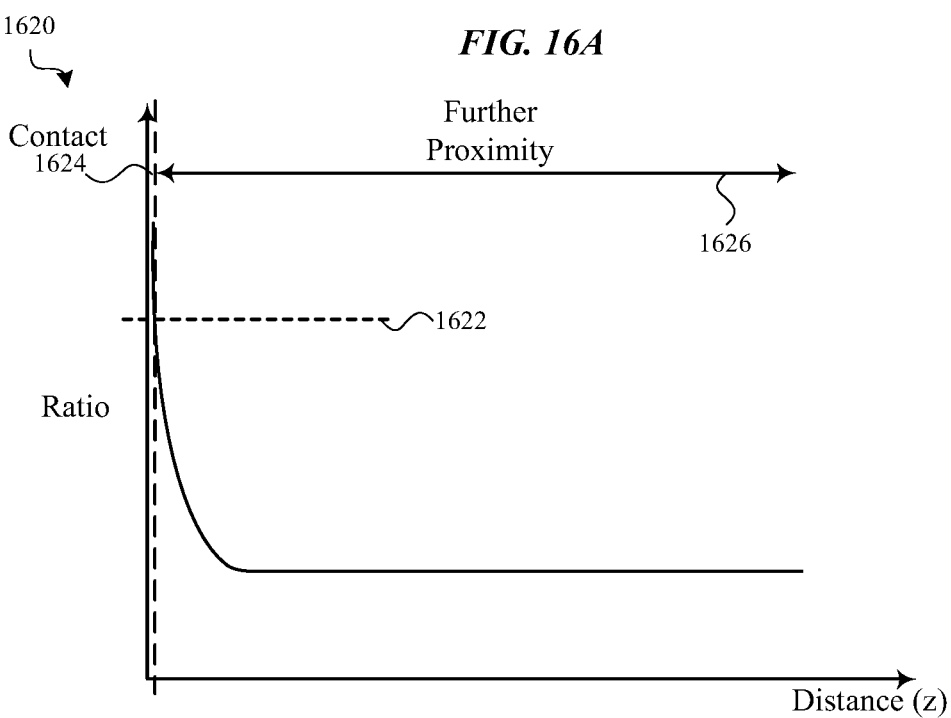

FIGS. 16A and 16B show example relationships between the measurements of the proximity sensors described with reference to FIGS. 13A-13B. As shown in FIG. 16A, and by way of example, a first proximity sensor may have a response 1602 that tapers off more quickly as an object moves farther away from the first proximity sensor, and a second proximity sensor may have a response 1604 that tapers off more slowly as an object moves farther away from the second proximity sensor. The first proximity sensor may therefore be useful to detect when an object is in close proximity 1606 (e.g., within a first range of proximities) and the second proximity sensor may be useful to detect when an object is in further proximity 1608 (e.g., within a second range of proximities that is more distant than the first range of proximities), or within the close or further proximity 1606, 1608. However, if the second proximity sensor is able to detect an object within the further proximity by consuming more power than the first proximity sensor, the second proximity sensor may be selectively enabled, as described with reference to FIG. 15A or 15B, thereby conserving power. A boundary 1610 between the close and further proximity 1606, 1608 may be defined as described with reference to FIG. 15A or 15B.

As shown in FIG. 16A, the first and second proximity sensors may have responses 1600 that approach a common asymptote within a first range of proximities, such as when an object is in contact with (or in near contact with) a device. A comparison of the measurements of the proximity sensors (e.g., a ratio or difference) may therefore provide an additional check that can be used to confirm whether the object is, in fact, within the first proximity range (e.g., that the object is in contact with the device). An example ratio 1620 of measurements of first and second proximity sensors is shown in FIG. 16B. When the ratio 1620 is closer to 1.0, or above a threshold 1622, the object may be considered in contact with the device (i.e., in a contact zone 1624). When the ratio 1620 drops below the threshold 1622, the object may be considered not in contact with the device (i.e., within a further proximity range 1626).

Figure 17A:
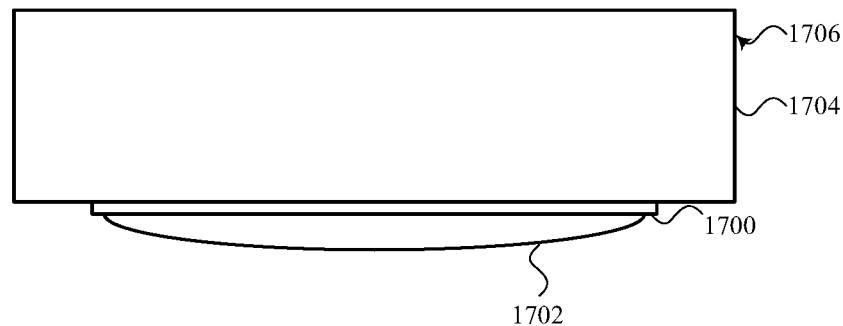
FIGS. 17A-17C show examples of proximity sensors that may be used as the first proximity sensor in the systems and devices described with reference to FIGS. 13A-14B.
Figure 17B:
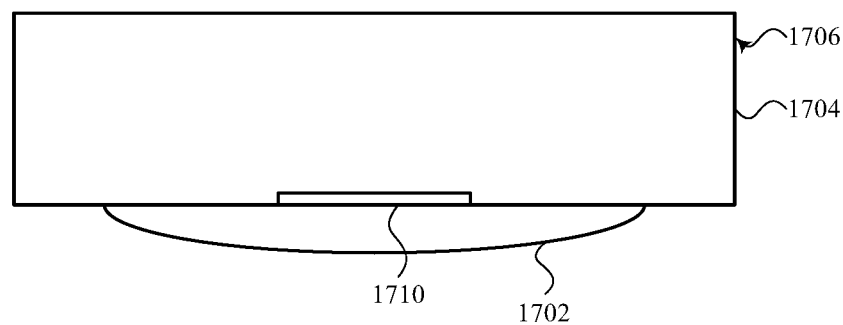
Figure 17C:
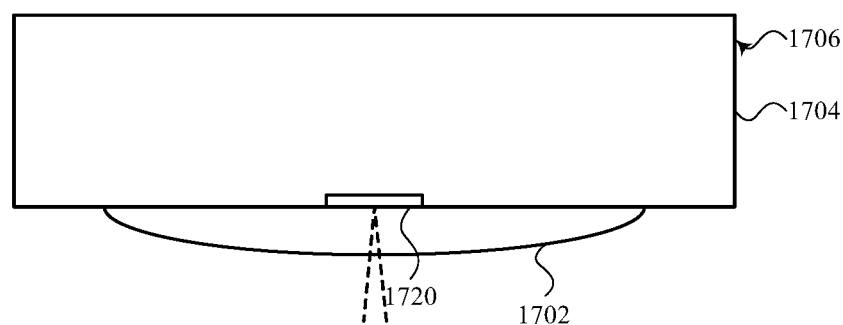

FIGS. 17A-17C show examples of proximity sensors that may be used as the first proximity sensor in the systems and devices described with reference to FIGS. 13A-14B. In some cases, the proximity sensors shown in FIGS. 17B and 17C may also or alternatively be used as the second proximity sensor in the systems and devices described with reference to FIGS. 13A-14B.

FIG. 17A shows an example of a pressure sensor 1700 (or load cell). The pressure sensor 1700 may be positioned between a back cover 1702 and frame 1704 of a housing 1706, and in some embodiments may include a force-sensitive gasket including first and second electrodes that move closer to one another and generate a series of measurements (e.g., capacitive-based pressure measurements) as the back cover 1702 is moved toward the frame 1704. For example, when a user fastens a device including the housing 1706 to their wrist using a band (e.g., a wrist band), their wrist may apply pressure to the back cover 1702 and press it toward the frame 1704.

In alternative embodiments, the pressure sensor 1700 may include a force-sensitive gasket having an air-filled pocket, fluid-filled pocket, or the like, and the pressure sensor 1700 may generate a series of pressure measurements indicating the pressure of the air or fluid within the pocket. In other alternative embodiments, the pressure sensor 1700 may be moved to a cavity within the frame 1704 and/or interior to a device that includes the housing 1706. For example, an air or fluid-filled cavity may be positioned interior to the device, and pressure on the back cover 1702 may impart changes to the pressure of the air or fluid within the cavity.

The pressure sensor 1700 described with reference to FIG. 17A may be considered a contact sensor, because an object needs to be in contact with the sensor before the sensor can detect a presence (or proximity) of the object. The range of object proximities that is detectable by a contact sensor corresponds to a range of movement of the contact sensor. Other types of contact sensor that may be used in place of, or in combination with, the pressure sensor 1700 include resistive sensors, bending beam sensors, and so on.

FIG. 17B shows an example of a capacitive sensor 1710. The capacitive sensor 1710 may be a self-capacitance sensor (having at least one sense electrode) or a mutual-capacitance sensor (having at least one sense electrode and at least one drive electrode). By way of example, a self-capacitance sensor is shown. In contrast to the pressure sensor described with reference to FIG. 17A, the capacitive sensor 1710 may detect an object (e.g., a user's wrist) before the object contacts the capacitive sensor 1710. In some embodiments, the capacitive sensor 1710 may generate a series of measurements (e.g., capacitance measurements) as it approaches the back cover 1702 and possibly comes into contact with the back cover 1702. In some embodiments, the capacitive sensor 1710 may detect a user within a range of proximities extending from about 0-5 mm from the back cover 1702.

FIG. 17C shows an example of an optical sensor 1720. The optical sensor 1720 may be disposed within the housing 1706, and in some cases may be attached to an interior surface of the back cover 1702 (or to a module that is attached to the interior surface of the back cover 1702). In some embodiments, one or more optic elements (e.g., a lens, lenses, LCF(s), polarizer(s), light guide(s), electromagnetic radiation waveguide(s), or other passive or active component) may be positioned between the optical sensor 1720 and the back cover 1702, or formed into the back cover 1702. In some embodiments, the optical sensor 1720 may generate a series of measurements (e.g., optical measurements) as it approaches the back cover 1702 and possibly comes into contact with the back cover 1702. The optical sensor 1720 may in some cases have a greater proximity detection range than the pressure sensor or capacitive sensor described with reference to FIG. 17A or 17B.

Figure 18:
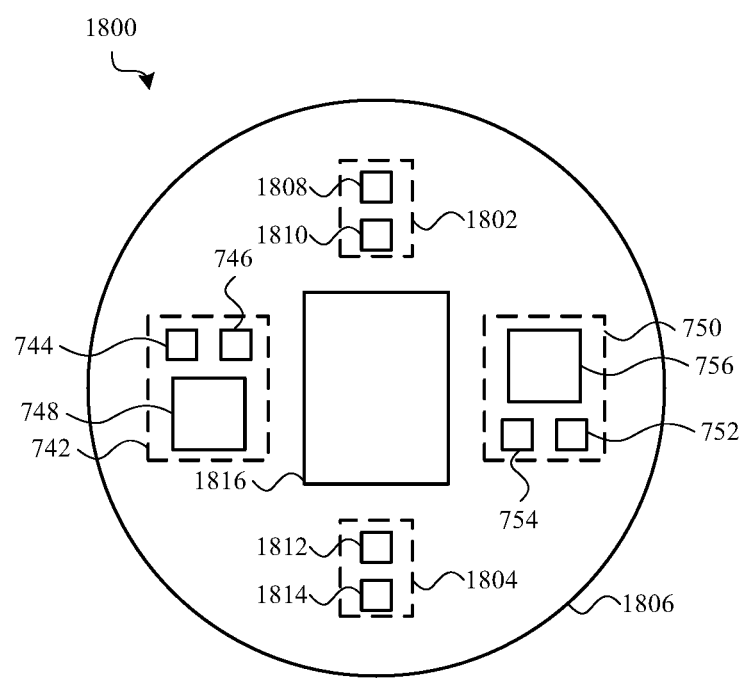
FIG. 18 shows an example plan view of a device in which multiple groups of proximity sensors are distributed about the back or back cover of the device's housing.

FIG. 18 shows an example plan view of a skin-facing sensor (or sensor system 1800) that may be included in the device described with reference to FIG. 1, 2A-2B, 4A-4B, 13A-13B, or 14A-14C. By way of example, the sensor system 1800 is shown to be positioned under a back or back cover 1806 of a housing (e.g., under the second back cover portion described with reference to FIG. 2B).

The sensor system 1800 includes multiple groups 1802, 1804 of proximity sensors distributed about different locations under the back or back cover 1806. In some embodiments, a first group 1802 of proximity sensors may include a first proximity sensor 1808 and a second proximity sensor 1810, and a second group 1804 of proximity sensors may include a third proximity sensor 1812 and a fourth proximity sensor 1814. The first and second proximity sensors 1808, 1810 may be respectively configured similarly to the first and second proximity sensors described with reference to FIGS. 13A-13B, but for their positions with respect to the exterior surface of the back cover 1806. The third and fourth proximity sensors 1812, 1814 may also be respectively configured similarly to the first and second proximity sensors described with reference to FIGS. 13A-13B, but for their positions with respect to the exterior surface of the back cover 1806.

In some embodiments, the proximity sensors 1808, 1810, 1812, 1814 may be connected to circuitry 1816 (e.g., a processor and/or other circuitry, which in some cases may include the processor described with reference to FIG. 1 or 2A-2B, or the circuitry described with reference to FIG. 3A-3B, 4A-4B, 13A-13B, or 14A-14C) that includes, or is configured to operate as, a proximity sensor management circuit. The proximity sensor management circuit may be configured to activate each of the first and third proximity sensors 1808, 1812 repeatedly or continually over a period of time, to generate first and third series of measurements indicating whether an object (e.g., a wrist of a user) is within the first range of proximities. By default, the proximity sensor management circuit may maintain the second and fourth proximity sensors 1810, 1814 in an inactive state. The proximity sensor management circuit may selectively activate the second proximity sensor 1810, during the period of time in which the first proximity sensor 1808 is active, when the series of measurements generated by the first proximity sensor 1808 satisfy a set of one or more conditions. Similarly, the proximity sensor management circuit may selectively deactivate the second proximity sensor 1810, during the period of time in which the first proximity sensor 1808 is active, when the series of measurements generated by the first proximity sensor 1808 or the second proximity sensor 1810 satisfy a second or third set of one or more conditions. The proximity sensor management circuit may selectively activate the fourth proximity sensor 1814, during the period of time in which the third proximity sensor 1812 is active, when the series of measurements generated by the third proximity sensor 1812 satisfy a set of one or more conditions. Similarly, the proximity sensor management circuit may selectively deactivate the fourth proximity sensor 1814, during the period of time in which the third proximity sensor 1812 is active, when the series of measurements generated by the third proximity sensor 1812 or the fourth proximity sensor 1814 satisfy the second or third set of one or more conditions. Selective activation/deactivation of the second and fourth proximity sensors 1810, 1814 may be useful, for example, when the second and fourth proximity sensors 1810, 1814 consume more power when activated (or in use) than the first and third proximity sensors 1808, 1812 consume when activated (or in use).

In some cases, the circuitry 1816 (e.g., a processor of the circuitry 1816) may be configured to indicate a tilt of the device (e.g., a watch body of an electronic watch) that includes the proximity sensors 1808, 1810, 1812, 1814. The tilt may in some cases be determined with respect to an object (e.g., a wrist to which the device is attached using a wrist band).

In some embodiments, the sensor system 1800 may further include a set of electromagnetic radiation emitters and one or more photodetectors that are usable to determine whether the back or back cover 1806 is likely proximate to human tissue. For example, the sensor system 1800 may include the two groups of sensing components described with reference to FIG. 7C or FIGS. 9A-9B (e.g., a first group 742 including a first emitter 744, a second emitter 746, and a first photodetector 748; and a second group 750 including a third emitter 752, a fourth emitter 754, and a second photodetector 756). In some cases, a matter differentiation circuit provided by the circuitry 1816 may only operate, or may determine which of the first photodetector 748 and/or the second photodetector 756 is likely outputting valid signals; or may interpret the signals output by the first photodetector 748 and/or the second photodetector 756, in response to whether the groups 1802, 1804 of proximity sensors indicate the back or back cover 1806 is positioned squarely above an object or tilted with respect to the object. In some cases, the first and third proximity sensors 1808, 1812 may not be activated until one or both of the groups 742, 750 of sensing components indicate the back or back cover 1806 is likely proximate human tissue. The groups 1802, 1804, 742, 750 of sensing components may also be used cooperatively, or separately, in other ways.

Figure 19:
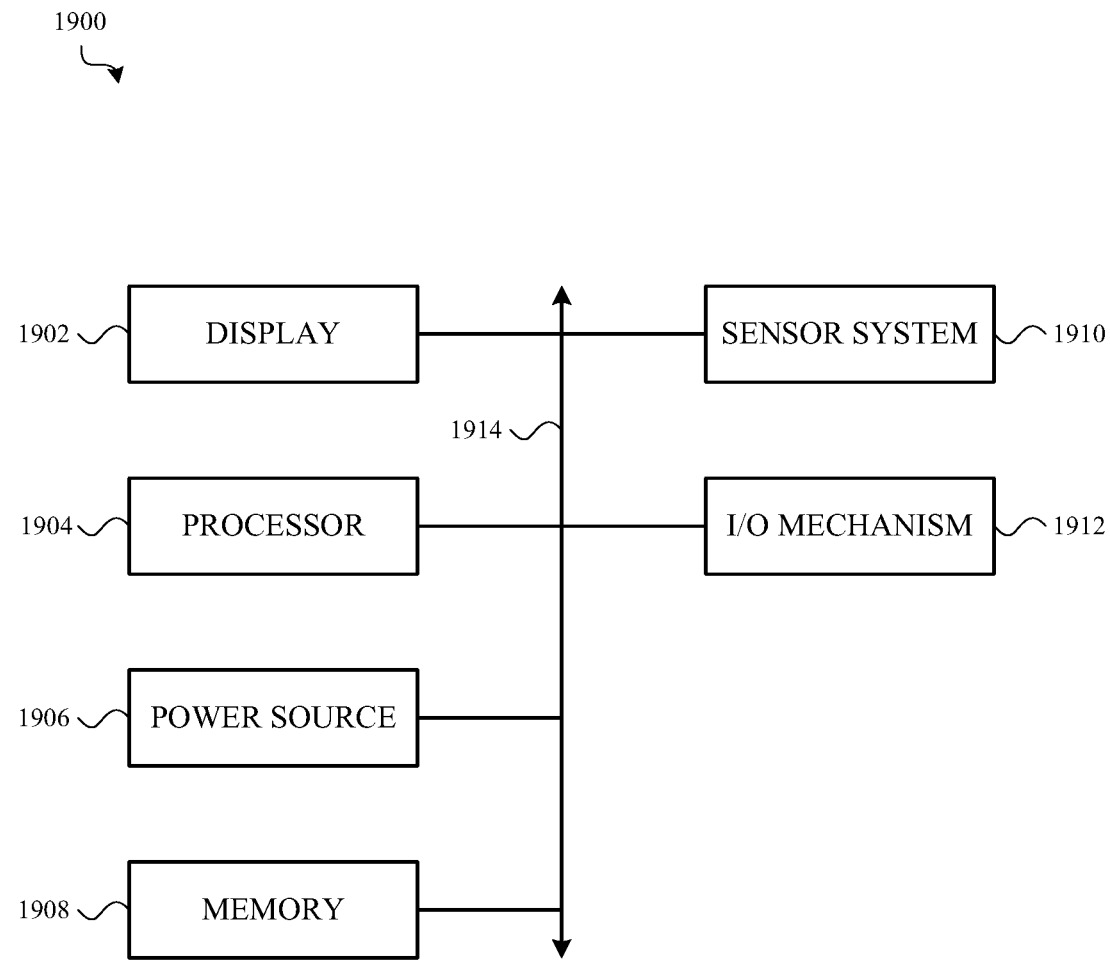
FIG. 19 shows a sample electrical block diagram of an electronic device, which electronic device may in some cases be implemented as any of the devices described with reference to FIG. 1, 2A-2B, 4A-4B, 13A-13B, or 14A-14C.

FIG. 19 shows a sample electrical block diagram of an electronic device 1900, which electronic device may in some cases be implemented as any of the devices described with reference to FIG. 1, 2A-2B, 4A-4B, 13A-13B, or 14A-14C. The electronic device 1900 may include an electronic display 1902 (e.g., a light-emitting display), a processor 1904, a power source 1906, a memory 1908 or storage device, a sensor system 1910, or an input/output (I/O) mechanism 1912 (e.g., an input/output device, input/output port, or haptic input/output interface). The processor 1904 may control some or all of the operations of the electronic device 1900. The processor 1904 may communicate, either directly or indirectly, with some or all of the other components of the electronic device 1900. For example, a system bus or other communication mechanism 1914 can provide communication between the electronic display 1902, the processor 1904, the power source 1906, the memory 1908, the sensor system 1910, and the I/O mechanism 1912.

The processor 1904 may be implemented as any electronic device capable of processing, receiving, or transmitting data or instructions, whether such data or instructions is in the form of software or firmware or otherwise encoded. For example, the processor 1904 may include a microprocessor, a central processing unit (CPU), an application-specific integrated circuit (ASIC), a digital signal processor (DSP), a controller, or a combination of such devices. As described herein, the term "processor" is meant to encompass a single processor or processing unit, multiple processors, multiple processing units, or other suitably configured computing element or elements. In some cases, the processor 1904 may provide part or all of the circuitry described with reference to any of FIG. 1-4B, 7A-14C, or 17A-18.

It should be noted that the components of the electronic device 1900 can be controlled by multiple processors. For example, select components of the electronic device 1900 (e.g., the sensor system 1910) may be controlled by a first processor and other components of the electronic device 1900 (e.g., the electronic display 1902) may be controlled by a second processor, where the first and second processors may or may not be in communication with each other.

The power source 1906 can be implemented with any device capable of providing energy to the electronic device 1900. For example, the power source 1906 may include one or more batteries or rechargeable batteries. Additionally or alternatively, the power source 1906 may include a power connector or power cord that connects the electronic device 1900 to another power source, such as a wall outlet.

The memory 1908 may store electronic data that can be used by the electronic device 1900. For example, the memory 1908 may store electrical data or content such as, for example, audio and video files, documents and applications, device settings and user preferences, timing signals, control signals, and data structures or databases. The memory 1908 may include any type of memory. By way of example only, the memory 1908 may include random access memory, read-only memory, Flash memory, removable memory, other types of storage elements, or combinations of such memory types.

The electronic device 1900 may also include one or more sensor systems 1910 positioned almost anywhere on the electronic device 1900. In some cases, the sensor systems 1910 may include one or more electromagnetic radiation emitters and detectors, and/or one or more proximity sensors, positioned as described with reference to any of FIG. 1-4B, 7A-14C, or 17A-18. The sensor system(s) 1910 may be configured to sense one or more type of parameters, such as but not limited to, vibration; light; touch; force; heat; movement; relative motion; biometric data (e.g., biological parameters) of a user; air quality; proximity; position; connectedness; matter type; and so on. By way of example, the sensor system(s) 1910 may include one or more of (or multiple of) a heat sensor, a position sensor, a proximity sensor, a light or optical sensor (e.g., an electromagnetic radiation emitter and/or detector), an accelerometer, a pressure transducer, a gyroscope, a magnetometer, a health monitoring sensor, and an air quality sensor, and so on. Additionally, the one or more sensor systems 1910 may utilize any suitable sensing technology, including, but not limited to, interferometric, magnetic, pressure, capacitive, ultrasonic, resistive, optical, acoustic, piezoelectric, or thermal technologies.

The I/O mechanism 1912 may transmit or receive data from a user or another electronic device. The I/O mechanism 1912 may include the electronic display 1902, a touch sensing input surface, a crown, one or more buttons (e.g., a graphical user interface "home" button), one or more cameras (including an under-display camera), one or more microphones or speakers, one or more ports such as a microphone port, and/or a keyboard. Additionally or alternatively, the I/O mechanism 1912 may transmit electronic signals via a communications interface, such as a wireless, wired, and/or optical communications interface. Examples of wireless and wired communications interfaces include, but are not limited to, cellular and Wi-Fi communications interfaces.

The foregoing description, for purposes of explanation, uses specific nomenclature to provide a thorough understanding of the described embodiments. However, it will be apparent to one skilled in the art, after reading this description, that the specific details are not required in order to practice the described embodiments. Thus, the foregoing descriptions of the specific embodiments described herein are presented for purposes of illustration and description. They are not targeted to be exhaustive or to limit the embodiments to the precise forms disclosed. It will be apparent to one of ordinary skill in the art, after reading this description, that many modifications and variations are possible in view of the above teachings.

As described above, one aspect of the present technology is the gathering and use of data available from various sources, including biometric data (e.g., the presence and/or proximity of a user to a device). The present disclosure contemplates that, in some instances, this gathered data may include personal information data that uniquely identifies or can be used to identify, locate, or contact a specific person. Such personal information data can include demographic data, location-based data, telephone numbers, email addresses, home addresses, data or records relating to a user's health or level of fitness (e.g., vital signs measurements, medication information, exercise information), date of birth, or any other identifying or personal information.

The present disclosure recognizes that the use of such personal information data, in the present technology, can be used to the benefit of users. For example, the personal information data can be used to activate or deactivate various functions of the user's device, or gather performance metrics for the user's device or the user. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act (HIPAA); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of advertisement delivery services, the present technology can be configured to allow users to select to "opt in" or "opt out" of participation in the collection of personal information data during registration for services or anytime thereafter. In another example, users can select not to provide mood-associated data for targeted content delivery services. In yet another example, users can select to limit the length of time mood-associated data is maintained or entirely prohibit the development of a baseline mood profile. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data at a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, content can be selected and delivered to users by inferring preferences based on non-personal information data or a bare minimum amount of personal information, such as the content being requested by the device associated with a user, other non-personal information available to the content delivery services, or publicly available information.

What is claimed is:

1. A wearable device, comprising:
a housing;
a wrist band attached to the housing;
a first emitter positioned within the housing and configured to emit, through a back of the housing, a first beam of electromagnetic radiation having a first infrared (IR)

wavelength selected from a near-infrared (NIR) band ranging from 750 nanometer (nm) to 1400 nm;

a second emitter positioned within the housing and configured to emit, through the back of the housing, a second beam of electromagnetic radiation having a second IR wavelength selected from a short-wavelength infrared (SWIR) band ranging from 1400 nm to 2000 nm, wherein the second IR wavelength is different from the first IR wavelength;

a photodetector positioned within the housing and filtered to detect a set of electromagnetic radiation wavelengths including the first IR wavelength and the second IR wavelength; and a matter differentiation circuit configured to indicate, at least partly in response to signals indicating amounts of the first IR wavelength and the second IR wavelength received by the photodetector, whether the back of the housing is likely proximate to a human tissue.

2. The wearable device of claim 1, wherein:

the first IR wavelength has a first human tissue reflectance factor;

the second IR wavelength has a second human tissue reflectance factor; and the first human tissue reflectance factor is different from the second human tissue reflectance factor.

3. The wearable device of claim 1, wherein:

the housing comprises a back cover through which the first emitter emits the first beam of electromagnetic radiation and the second emitter emits the second beam of electromagnetic radiation; and the first emitter, the second emitter, and the photodetector are adhesively attached to an interior surface of the back cover, apart from other components of the housing.

4. The wearable device of claim 3, wherein an exterior surface of the back cover has an arcuate profile.

5. The wearable device of claim 3, wherein each of the first emitter, the second emitter, and the photodetector is positioned off-axis with respect to a center axis of the back cover, the center axis is perpendicular to an exterior surface of the back cover.

6. The wearable device of claim 5, wherein the photodetector is a first photodetector, the wearable device further comprising:

a third emitter positioned within the housing and configured to emit, through the back cover, a third beam of electromagnetic radiation having the first IR wavelength;

a fourth emitter positioned within the housing and configured to emit, through the back cover, a fourth beam of electromagnetic radiation having the second IR wavelength; and a second photodetector positioned within the housing and filtered to detect a set of wavelengths including the first IR wavelength and the second IR wavelength; wherein:

the first photodetector is grouped with the first and second emitters;

the second photodetector is grouped with the third and fourth emitters, with each of the third emitter, the fourth emitter, and the second photodetector positioned off-axis with respect to the center axis of the back cover; and the matter differentiation circuit is further configured to indicate whether the back of the housing is likely proximate to the human tissue at least partly in response to signals indicating amounts of the first IR wavelength and the second IR wavelength received by the second photodetector.

7. The wearable device of claim 1, further comprising:

a set of one or more infrared wavelength-blocking walls disposed between the photodetector and each of the first and second emitters.

8. The wearable device of claim 1, wherein the photodetector is a first photodetector, the wearable device further comprising:

a second photodetector positioned within the housing and filtered to detect a set of wavelengths including the first IR wavelength and the second IR wavelength; wherein:

the matter differentiation circuit is further configured to indicate whether the back of the housing is likely proximate to the human tissue at least partly in response to signals indicating amounts of the first IR wavelength and the second IR wavelength received by the second photodetector.

9. The wearable device of claim 1, further comprising:

a third emitter positioned within the housing and configured to emit, through the back of the housing, a third beam of electromagnetic radiation having a wavelength different from the first IR wavelength and the second IR wavelength; wherein:

the photodetector is further filtered to detect the wavelength of the third beam of electromagnetic radiation; and the matter differentiation circuit is further configured to indicate whether the back of the housing is likely proximate to the human tissue at least partly in response to a signal indicating an amount of the wavelength of the third beam of electromagnetic radiation received by the photodetector.

10. The wearable device of claim 9, wherein one of the first, second, or third emitters is configured to, at least one of:

emit a different size beam of electromagnetic radiation than the other emitters;

be operated at a different optical power than the other emitters; or have an electromagnetic radiation-emitting aperture positioned at different distances from a centroid of the photodetector.

11. The wearable device of claim 1, further comprising:

a Fresnel lens positioned between the housing and at least one of the first emitter, the second emitter, or the photodetector.

12. The wearable device of claim 1, further comprising:

a light control film (LCF) positioned between the housing and at least one of the first emitter, the second emitter, or the photodetector.

13. A device, comprising:

a first emitter configured to emit a first beam of electromagnetic radiation of a first wavelength toward an object, the first wavelength in a near-infrared (NIR) band ranging from 750 nanometer (nm) to 1400 nm;

a second emitter configured to emit a second beam of electromagnetic radiation of a second wavelength toward the object, the second wavelength in a short-wavelength infrared (SWIR) band ranging from 1400 nm to 2000 nm, wherein the first beam of electromagnetic radiation and the second beam of electromagnetic radiation have different human tissue reflectance factors, and the first wavelength is different from the second wavelength;

a photodetector filtered to detect a first notch of the first wavelength and a second notch of the second wavelength;

a timing circuit configured to operate the first emitter and the second emitter, to respectively emit the first beam of electromagnetic radiation or the second beam of electromagnetic radiation at different times; and a matter differentiation circuit configured to indicate whether the device is likely proximate to a human tissue, the indication based at least partly on:

the first notch of the first wavelength detected by the photodetector after the first emitter emits the first beam; and the second notch of the second wavelength detected by the photodetector after the second emitter emits the second beam.

14. The device of claim 13, wherein the indication is based at least partly on a ratio of a first amount of electromagnetic radiation detected by the photodetector after the first emitter emits the first beam to a second amount of electromagnetic radiation detected by the photodetector after the second emitter emits the second beam.

15. The device of claim 14, wherein the matter differentiation circuit is configured to compare the ratio to a threshold, and only indicate the device is likely proximate to the human tissue when the ratio satisfies the threshold.

16. The device of claim 15, further comprising:

a distance detector configured to detect a distance between the device and the object; wherein, the matter differentiation circuit is configured to adjust the threshold in response to the detected distance.

17. The device of claim 13, wherein the indication is further based at least partly on a relationship between the first amount of electromagnetic radiation, the second amount of electromagnetic radiation, and a ratio of the first amount of electromagnetic radiation to the second amount of electromagnetic radiation.

18. The device of claim 13, further comprising:

a proximity detection circuit configured to indicate a proximity of the device to the object, the proximity indication based at least in part on:

a first amount of electromagnetic radiation received by the photodetector after the first emitter emits the first beam; and a second amount of electromagnetic radiation received by the photodetector after the second emitter emits the second beam.

19. The device of claim 18, wherein the proximity indication identifies one of at least two different proximity ranges.

20. The device of claim 13, further comprising:

an electromagnetic radiation beam director positioned in a path of the second beam of electromagnetic radiation and configured to tilt an axis of the second beam of electromagnetic radiation away from the photodetector.

21. The device of claim 13, further comprising:

a power source; and a component configured to receive power from the power source; and a power conservation circuit configured to reduce power supplied to the component by the power source when the matter differentiation circuit indicates the device is not likely proximate to the human tissue.

22. The device of claim 13, further comprising:

a set of coatings or optical filter elements disposed over an aperture of at least one of the first emitter or the second emitter.

* * * * *